(12) United States Patent
Nori et al.

(10) Patent No.: US 11,537,818 B2
(45) Date of Patent: Dec. 27, 2022

(54) APPARATUS, COMPUTER PROGRAM PRODUCT, AND METHOD FOR PREDICTIVE DATA LABELLING USING A DUAL-PREDICTION MODEL SYSTEM

(71) Applicant: Optum, Inc., Minnetonka, MN (US)

(72) Inventors: Vijay S. Nori, Roswell, GA (US); Christopher A. Hane, Irvine, CA (US); Paul A. Bleicher, Newton, MA (US)

(73) Assignee: Optum, Inc., Minnetonka, MN (US)

( * ) Notice: Subject to any disclaimer, the term of this patent is extended or adjusted under 35 U.S.C. 154(b) by 212 days.

(21) Appl. No.: 16/746,232

(22) Filed: Jan. 17, 2020

(65) Prior Publication Data

US 2021/0224602 A1 Jul. 22, 2021

(51) Int. Cl.
*G06K 9/00* (2022.01)
*G06K 9/62* (2022.01)
(Continued)

(52) U.S. Cl.
CPC .......... *G06K 9/6259* (2013.01); *G06F 17/16* (2013.01); *G06K 9/6277* (2013.01); *G06N 20/00* (2019.01)

(58) Field of Classification Search
CPC .. G06K 9/6259; G06K 9/6277; G06K 9/6256; G06F 17/16; G06N 20/00; G06N 7/005; G16H 50/20; G16H 50/30
See application file for complete search history.

(56) References Cited

U.S. PATENT DOCUMENTS

| 7,076,437 B1 | 7/2006 | Levy |
| 9,679,374 B2 | 6/2017 | Choi et al. |

(Continued)

FOREIGN PATENT DOCUMENTS

| AU | 1238501 A | 5/2001 |
| AU | 2014311712 A1 | 3/2016 |

(Continued)

OTHER PUBLICATIONS

AlzheimersAssociation, 2017 Alzheimer's Disease Facts and Figures. 2017:325-373.
(Continued)

*Primary Examiner* — Dhaval V Patel
(74) *Attorney, Agent, or Firm* — Alston & Bird LLP

(57) ABSTRACT

Various embodiments of the disclosure provide apparatuses, systems, and computer program products for predictive data labelling using a dual-model system. Embodiments provide various advantages in accuracy of predicted labels, for example in various contexts such as medical data analysis for difficult to diagnose diseases. An example provided apparatus is configured to generate a positive, neutral, and negative candidate identifier sets and corresponding positive, neutral, and negative candidate index sets based in part on applying a candidate selection rule set to a candidate data set; train a candidate label probabilistic model based at least in part on a candidate label training subset associated with the candidate data set associated with the positive and negative candidate identifiers; generate a candidate positive-label probability set using at least the candidate label probabilistic model; train a historical record prediction model to predict the candidate positive-label probability set; and utilize the historical record prediction model.

20 Claims, 12 Drawing Sheets

(51) Int. Cl.
  *G06F 17/16* (2006.01)
  *G06N 20/00* (2019.01)

(56) References Cited

U.S. PATENT DOCUMENTS

| | | | |
|---|---|---|---|
| 9,805,463 | B2 | 10/2017 | Choi et al. |
| 10,096,104 | B2 | 10/2018 | Choi et al. |
| 2008/0221927 | A1 | 9/2008 | Levy |
| 2009/0299977 | A1 | 12/2009 | Rosales |
| 2015/0065846 | A1 | 3/2015 | Choi et al. |
| 2015/0065847 | A1 | 3/2015 | Choi et al. |
| 2015/0065848 | A1 | 3/2015 | Choi et al. |
| 2015/0066818 | A1 | 3/2015 | Choi et al. |
| 2016/0300026 | A1 | 10/2016 | Bogoni et al. |
| 2016/0300350 | A1 | 10/2016 | Choi et al. |
| 2018/0101652 | A1 | 4/2018 | Kochura et al. |
| 2018/0101657 | A1 | 4/2018 | Kochura et al. |
| 2018/0300640 | A1* | 10/2018 | Birnbaum ............ G16H 10/60 |
| 2018/0315182 | A1 | 11/2018 | Rapaka et al. |
| 2018/0365381 | A1 | 12/2018 | Tang et al. |
| 2018/0366222 | A1* | 12/2018 | Tang ..................... G16H 50/20 |
| 2019/0019289 | A1 | 1/2019 | Choi et al. |
| 2019/0108912 | A1 | 4/2019 | Spurlock et al. |
| 2019/0108915 | A1* | 4/2019 | Spurlock, III ..... C07K 16/2866 |
| 2020/0257992 | A1* | 8/2020 | Achin ..................... G06N 20/10 |

FOREIGN PATENT DOCUMENTS

| | | | |
|---|---|---|---|
| CA | 2922303 | A1 | 3/2015 |
| CN | 104915560 | A | 9/2015 |
| CN | 105518684 | A | 4/2016 |
| CN | 108784655 | A | 11/2018 |
| CN | 109147931 | A | 1/2019 |
| EP | 2987105 | A2 | 2/2016 |
| EP | 3404666 | A2 | 11/2018 |
| JP | 2016-529037 | A | 9/2016 |
| JP | 6140900 | B2 | 6/2017 |
| KR | 2016-0047516 | A | 5/2016 |
| TW | 201905838 | A | 2/2019 |
| TW | 201905839 | A | 2/2019 |
| TW | I656503 | B | 4/2019 |
| WO | 01/33378 | A1 | 5/2001 |
| WO | 2015/030998 | A2 | 3/2015 |
| WO | 2019/071098 | A2 | 4/2019 |

OTHER PUBLICATIONS

Appendix A Data Set Creation.
Appendix C. Analytic Methods.
Emanuel, E. et al., "The Cost of Conducting Clinical Research", Journal of Clinical Oncology, vol. 22, No. 22, dated Nov. 15, 2003.
Hebert, L.E., et al., Alzheimer disease in the United States (2010-2050) estimated using the 2010 census. Neurology 2013;80(19):1778-1783.
Hebert, L.E., et al., Annual Incidence of Alzheimer Disease in the United States Projected to the Years 2000 Through 2050. Alzheimer Disease & Associated Disorders 2001;15(4):169-173.
King, Gary et al., "Logistic Regression in Rare Events Data", dated Feb. 16, 2001.
Natarajan, N. et al., "Learning with Noisy Labels", Department of Computer Science, University of Texas, Austin, dated (2006).
Pearce, Neil. "Analysis of matched case-control studies", The BMJ, dated Feb. 25, 2016.
Prince, M., et al., The global prevalence of dementia: A systematic review and metaanalysis. Alzheimer's & Dementia 2013;9(1):63-75.e2.
Vijay, S Nori et al., "Identifying incident dementia by applying machine learning to a very large administrative claims dataset", dated Aug. 20, 2018.
Vijay, S Nori et al., "Machine Learning Models to Predict Onset of Dementia: A Label Learning Approach" dated Jun. 19, 2019.

* cited by examiner

APPARATUS, COMPUTER PROGRAM PRODUCT, AND METHOD FOR PREDICTIVE DATA LABELLING USING A DUAL-PREDICTION MODEL SYSTEM

TECHNOLOGICAL FIELD

Embodiments of the present disclosure generally relate to predictive data labelling and, specifically, to predictive data labelling according to a defined ruleset using a dual-prediction model system.

BACKGROUND

Conventional systems for data labeling often utilize a defined source of truth. In such circumstances, training and/or labeling for complex tasks (e.g., where a definitive test is not readily available) may make it difficult to appropriately label data associated with various users. One such example context is in labelling users for the purposes of candidacy for a treatment, therapeutic, trial, or diagnostic intervention. A definitive diagnosis of a disease may represent different disease physiologies with a final shared clinical appearance, which makes identifying appropriate candidates for such treatment, therapeutic, trial, or diagnostic intervention difficult. Often, candidates that are not undoubtably into one camp or another (e.g., a case or a control) are discarded for the purposes of forming such cohorts. Applicant has discovered problems with conventional systems, methods, apparatuses, and computer program products for data labelling, and through applied effort, ingenuity, and innovation, Applicant has solved many of these identified problems by developing a solution that is embodied in the present disclosure, which is described in detail below.

BRIEF SUMMARY

In general, embodiments of the present disclosure provided herein include systems, methods, apparatuses and computer program products for data labelling according to a defined ruleset using a dual-prediction model system. Other systems, apparatuses, methods, computer readable media, and features will be, or will become, apparent to one with skill in the art upon examination of the following figures and detailed description. It is intended that all such additional systems, apparatuses, methods, computer readable media, and features be included within this description be within the scope of the disclosure, and be protected by the following claims.

In at least one example aspect of the present disclosure, a computer-implemented method for data labelling using a dual-prediction model system is provided. The computer-implemented method may be implemented using any of a number of computing implementations described herein, including in hardware, firmware, software, or a combination thereof. In at least one example embodiment, the computer-implemented method includes generating (1) a positive candidate identifier set and a positive candidate index set corresponding to the positive candidate identifier set, (2) a negative candidate identifier set and a negative candidate index set corresponding to the negative candidate identifier set, and (3) a neutral candidate identifier set and a neutral candidate index set corresponding to the neutral candidate identifier set, based in part on applying a candidate selection rule set to a candidate data set, where the candidate data set is associated with a candidate pool identifier set comprising the positive candidate identifier set, negative candidate identifier set, and neutral candidate identifier set. The example computer-implemented method further includes training a candidate label probabilistic model based at least in part on a candidate label training subset associated with the candidate data set, the candidate label training subset identified based on the positive candidate identifier set together with the positive candidate index set and a short-term record threshold, and the negative candidate identifier set together with the negative candidate index set and the short-term record threshold. The example computer-implemented method further includes generating a candidate positive-label probability set corresponding to the candidate pool identifier set based at least in part on applying an index-limited candidate data subset to the candidate label probabilistic model, where the index-limited candidate data subset is based on the positive candidate identifier set together with the positive candidate index set and the short-term record threshold, the negative candidate identifier set together with the negative candidate index set and the short-term record threshold, and the neutral candidate identifier set together with the neutral candidate index set and the short-term record threshold. The example computer-implemented method further includes training a historical record prediction model to predict the candidate positive-label probability set based at least in part on the candidate positive-label probability set and a long-term historical data subset associated with the candidate pool identifier set, where the long-term historical data subset is based on the positive candidate identifier set together with the positive candidate index set and a long-term record threshold, the negative candidate identifier set together with the negative candidate index set and the long-term record threshold, and the neutral candidate identifier set together with the neutral candidate index set and the long-term record threshold. The example computer-implemented method further includes utilizing the historical record prediction model to generate a long-term candidate positive-label probability associated with at least one candidate identifier.

Additionally or alternatively in some example embodiments of the computer-implemented method, the computer-implemented method further includes, for each positive candidate identifier of at least a subset of the positive candidate identifier set: identifying a positive candidate data subset, associated with the positive candidate identifier, from the candidate data set based at least on a positive candidate index date associated with the positive candidate identifier and the short-term record threshold; generating a positive candidate fact vector for the positive candidate identifier based on the positive candidate data subset for the positive candidate identifier, the positive candidate fact vector associated with a first learned label; and adding the positive candidate fact vector to the candidate label training subset. In some such example embodiments of the computer-implemented method, the computer-implemented method further includes, for each negative candidate identifier of at least a subset of the negative candidate identifier set: identifying a negative candidate data subset, associated with the negative candidate identifier, from the candidate data set based at least on a negative candidate index date associated with the negative candidate identifier and the short-term record threshold; generating a negative candidate fact vector for the positive candidate identifier based on the negative candidate data subset for the negative candidate identifier, the negative candidate fact vector associated with a second learned label; and adding the negative candidate fact vector to the candidate label training subset.

Additionally or alternatively in some example embodiments of the computer-implemented method, training the candidate label probabilistic model includes: identifying a positive candidate data record set of the candidate data set, wherein each data record of the positive candidate data record set is associated with a positive candidate identifier of the positive candidate identifier set; determining each data record of the positive candidate data record set is associated with a record timestamp on or before an index date associated with the positive candidate identifier of the positive candidate index set, and on or after a critical date based on the index date and the short-term record threshold; generating at least a portion of the candidate data training subset based on the positive candidate data record set; identifying a negative candidate data record set of the candidate data set, wherein each data record of negative candidate data record set is associated with a negative candidate identifier of the negative candidate identifier set; determining each data record of the negative candidate data record set is associated with a second record timestamp on or before a second index date associated with the negative candidate identifier of the negative candidate index set, and on or after a second critical date based on the second index date and the short-term record threshold; and generating at least a second portion of the candidate label training subset based on the negative candidate data record set.

Additionally or alternatively in some example embodiments of the computer-implemented method, training the candidate label probabilistic model includes: configuring the candidate label training subset by matching at least a positive candidate identifier of the positive candidate identifier set with a negative candidate identifier of the negative candidate identifier set based on at least one demographic property; and training the candidate label probabilistic model based on the configured candidate label training subset.

Additionally or alternatively in some example embodiments of the computer-implemented method, the computer-implemented method further includes identifying the candidate data set from one or more local datastores, one or more external datastores, or a combination thereof.

Additionally or alternatively in some example embodiments of the computer-implemented method, the candidate data set comprises a plurality of data records, each data record associated with a candidate identifier of the candidate pool identifier set and a services timestamp.

Additionally or alternatively in some example embodiments of the computer-implemented method, the candidate data set comprises a structured medical data record set, an unstructured medical data, or a combination thereof.

Additionally or alternatively in some example embodiments of the computer-implemented method, generating the negative candidate identifier set and the negative candidate index set comprises: identifying a candidate data subset associated with a candidate identifier of the candidate pool identifier set; upon determining, based on the candidate data, the candidate data subset does not satisfy any selection rule of the candidate selection rule set: adding a randomized index date associated with the candidate identifier to the negative candidate index set, the randomized index date based on the candidate data subset; and adding the candidate identifier to the negative candidate identifier set.

Additionally or alternatively in some example embodiments of the computer-implemented method, generating the neutral candidate identifier set and the neutral candidate index set comprises: identifying a candidate data subset associated with a candidate identifier of the candidate pool identifier; upon determining, based on the candidate data, the candidate data subset satisfies at least one selection rule of the candidate selection rule set but does not satisfy every selection rule of the candidate selection rule set: adding a most recent index date associated with the candidate identifier to the neutral candidate index set, the most recent index date based on the at least one satisfied candidate selection rule; and adding the candidate identifier to the neutral candidate identifier set.

Additionally or alternatively in some example embodiments of the computer-implemented method, generating the positive candidate identifier set and the positive candidate index set comprises: identifying a candidate data subset associated with a candidate identifier of the candidate pool identifier; upon determining, based on the candidate data, the candidate data subset satisfies at each selection rule of the candidate selection rule set: adding a most recent index date associated with the candidate identifier to the positive candidate index set, the most recent index date based on each satisfied candidate selection rule; and adding the candidate identifier to the positive candidate identifier set.

Additionally or alternatively in some example embodiments of the computer-implemented method, training the candidate label probabilistic model comprises: generating a positive candidate data set based on the candidate data set, the positive candidate identifier set, and the positive candidate index set; generating a negative candidate data set based on the candidate set, the negative candidate identifier set, and the negative candidate index set; generating the candidate label training subset at least in part by combining the positive candidate data set and the negative candidate data set; and training the candidate label probabilistic model based at least in part on the candidate label training subset.

Additionally or alternatively in some example embodiments of the computer-implemented method, utilizing the historical record prediction model to generate the candidate positive-label probability associated with at least one candidate identifier comprises: generating a historical record predictive score set at least in part by applying the candidate data set to the historical record prediction model.

Additionally or alternatively in some example embodiments of the computer-implemented method, applying the index-limited candidate data subset to the candidate label probabilistic model to determine the candidate positive-label probability set corresponding to candidate pool identifier set comprises: determining an unadjusted candidate positive-label probability set corresponding to candidate pool identifier set at least in part by applying the index-limited candidate data subset to the candidate label probabilistic model; for at least a candidate identifier in the candidate pool identifier set, wherein the candidate identifier is associated with an unadjusted positive-label probability from the unadjusted candidate positive-label probability set, determining a total score neighborhood count associated with the candidate identifier, the total score neighborhood count based on the unadjusted positive-label probability and a score adjustment range; determining a positive score neighborhood count associated with the candidate identifier, the positive score neighborhood count based on the unadjusted positive-label probability, the score adjustment range, and a positive-label probability threshold; and generating an adjusted candidate positive-label probability associated with the candidate identifier based at least in part on the total neighborhood count and the positive score neighborhood count, where the determined candidate positive-label probability set comprises at least one adjusted candidate positive-label probability. Additionally or alternatively, in some such embodiments of the computer-implemented method, the computer-implemented method further comprises applying the index-limited candidate data subset to the candidate label probabilistic model to determine an unadjusted candidate positive-label probability set corresponding to candidate pool identifier set; for at least a candidate identifier in the candidate pool identifier set, wherein the candidate identifier is associated with an unadjusted positive-label probability from the unadjusted candidate positive-label probability set, determining a first total score neighborhood count associated with the candidate identifier, the total score neighborhood count based on the unadjusted positive-label probability and a score adjustment range; determining the first total score neighborhood count does not satisfy a neighborhood count threshold; adjusting the score adjustment range by multiplying the score adjustment range with a score adjustment factor at least one time; determining an updated total score neighborhood count associated with the candidate identifier, the total score neighborhood count based on the unadjusted positive-label probability and a score adjustment range, where the updated total score neighborhood satisfies the neighborhood count threshold; determining a positive score neighborhood count associated with the candidate identifier, the positive score neighborhood count based on the unadjusted positive-label probability, the score adjustment range, and a positive-label probability threshold; and generating an adjusted candidate positive-label probability associated with the candidate identifier at least in part based on the updated total neighborhood count and the positive score neighborhood count, where the determined candidate positive-label probability set comprises at least one adjusted candidate positive-label probability.

In accordance with yet another aspect of the present disclosure, at least one apparatus for data labelling using a dual-prediction model system is provided. In at least one example embodiment, the apparatus comprises at least one processor and at least one non-transitory memory. The at least one non-transitory memory stores computer-coded instructions that, in execution with the at least one processor, configure the apparatus to perform one or more actions. In at least some example embodiment, the computer-coded instructions configure the apparatus to perform some or all operations of any of the computer-implemented methods described above.

In accordance with yet another aspect of the present disclosure, at least one computer program products for data labelling using a dual-prediction model system is provided. In at least one example embodiment, the computer program product comprises at least one non-transitory computer readable storage medium. The at least one non-transitory computer readable storage medium is configured to store computer program code thereon. The computer program code, in execution with at least one processor, is configured for performing some or all operations of any of the computer-implemented methods described above.

BRIEF DESCRIPTION OF THE DRAWINGS

Figure 1:
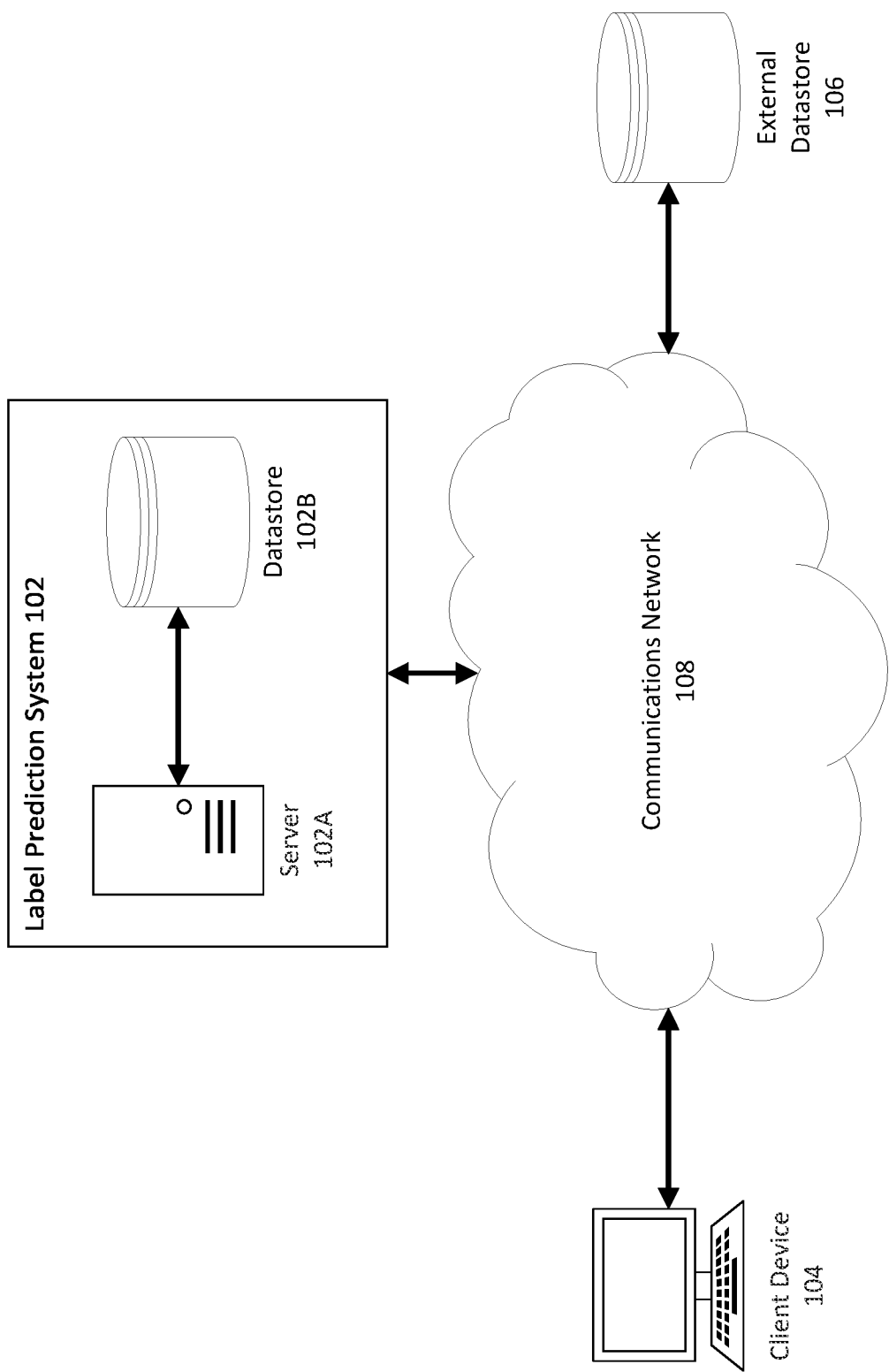
Figure 2:
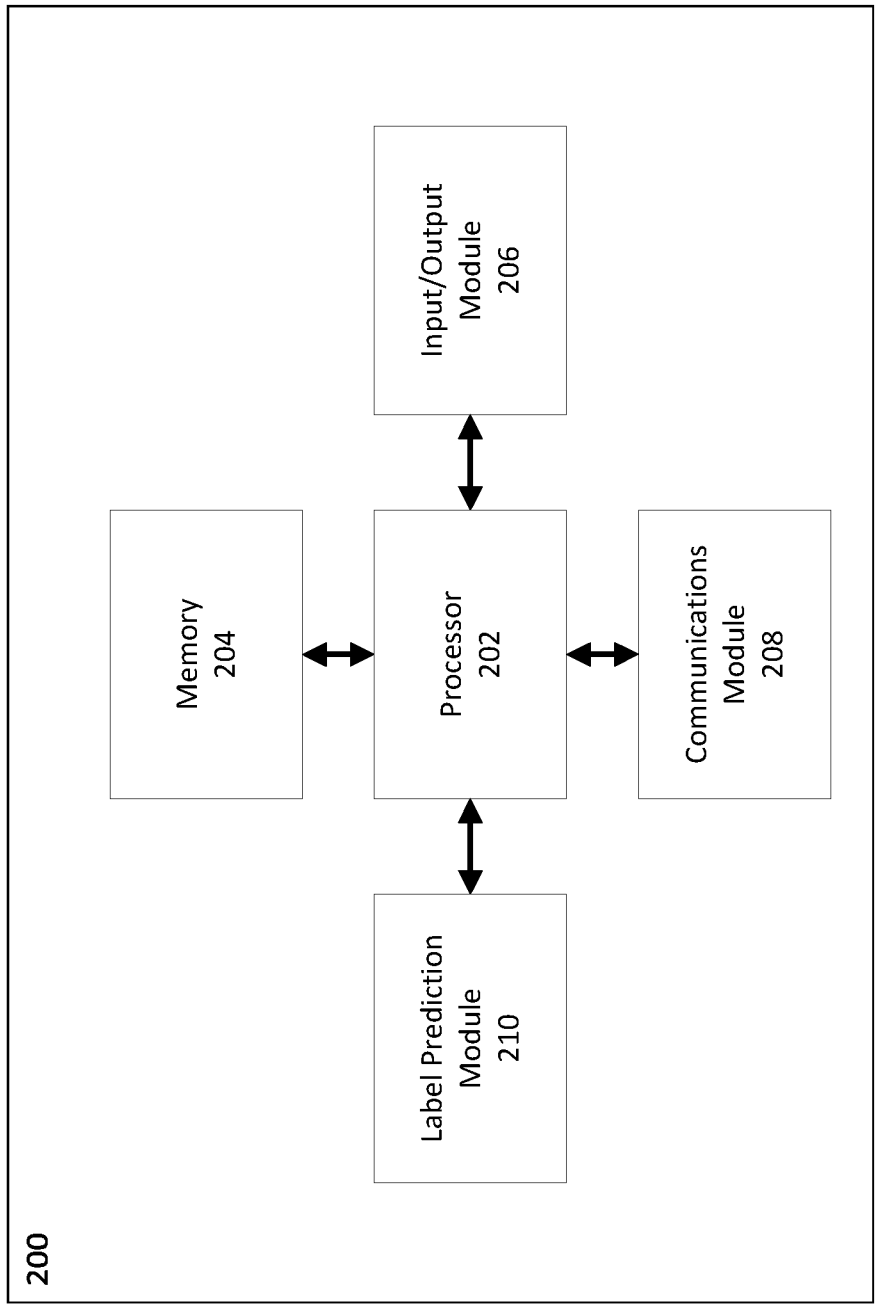
Figure 7:
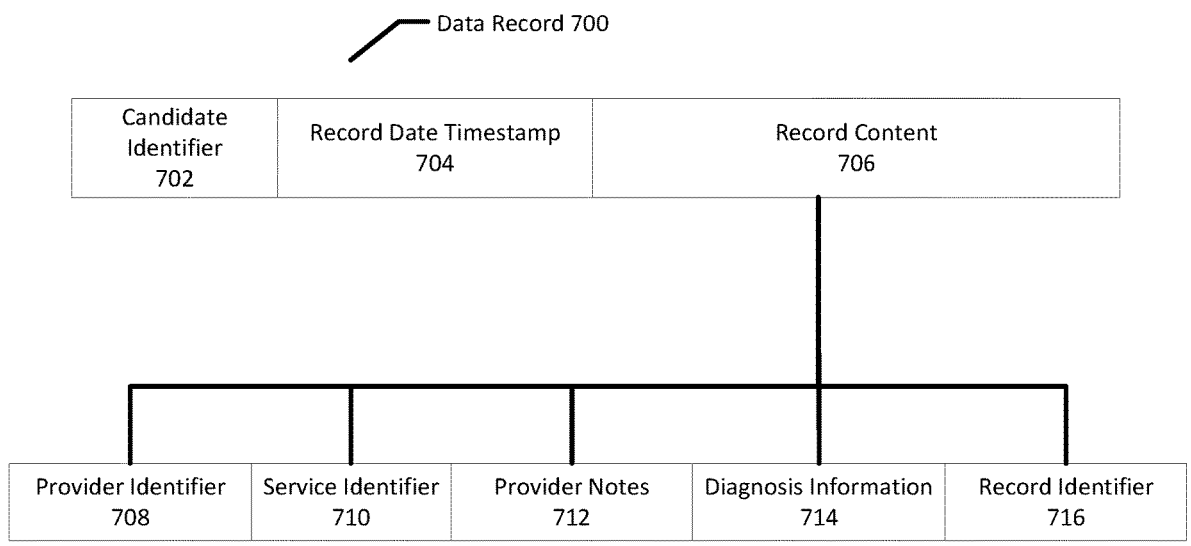

Having thus described the embodiments of the disclosure in general terms, reference now will be made to the accompanying drawings, which are not necessarily drawn to scale, and wherein:

FIG. 1 illustrates a block diagram of a system that may be specially configured within which embodiments of the present disclosure may operate;

FIG. 2 illustrates a block diagram of an example apparatus that may be specially configured in accordance with an example embodiment of the present disclosure;

FIGS. 3A, 3B and 4-6 illustrate an example computing environment and corresponding data flow in accordance with example embodiments of the present disclosure;

FIG. 7 illustrates an example data record in accordance with example embodiments of the present disclosure; and FIGS. 8-12 illustrate example flowcharts including operations for label predicting using a dual-model system in accordance with at least one example embodiments of the present disclosure.

DETAILED DESCRIPTION

Embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

Overview

Data labelling often relies on a definitive source of truth for classifying data associated with various users. For complex tasks that do not have an easily or consistently identifiable source of truth, this often leads such classification models and/or other methodologies to rely on users that definitively fall within a particular label based on the definitive source of truth. Often, this limits the number of users that may be used, and in some circumstances the number of users that do not fall definitively into one group or another is significant.

One example context where such conventional data labelling exemplifies such problems is in labelling candidates for treatment, therapeutic, trial, or diagnostic intervention for certain diseases. Many complex diseases lack a comprehensive test that can readily separate candidates into various groups. In the context of a randomized clinical trial ("RCT"), for example, difficult to diagnose diseases often lack consistent data labelling methodologies that can split candidates into cases (e.g., indicating the candidate should be diagnosed with the disease) and controls (e.g., indicating the candidate should not be diagnosed with the disease). Errors in data labelling can lead a candidate to wrongly being included in and/or excluded from an RCT, which in many instances is a costly and/or harmful, if not deadly, mistake. To avoid such mistakes, RCTs often target only the specific, limited population that may be definitively labelled as a case, for example satisfying every rule of a particular ruleset associated with the disease diagnosis, or a control, for example failing to satisfy any rule of the particular ruleset associated with the disease diagnosis. However, relying on such limited candidate pools lead to significant delays and/or clinical trial failures.

Additionally, such data labelling is vulnerable to variations in the defined source of truth. For example, if a diagnosis by a doctor or other healthcare professional is considered truth for purposes of labeling a candidate as a case or control, improper diagnoses cause unnecessary patient risk from placing a candidate in a clinical trial they should not be in. Alternatively, if one or more candidates is enrolled in a clinical trial but have a different subset of the disease, this may produce extra variation in RCT outcomes and/or in some instances, may lead the candidate to not respond to the treatment, further increasing risk to the entity managing the RCT. This problem associated with conventional data labeling methodologies further adds to patient risk and/or other problems associated with improper labeling. Furthermore, RCTs remain expensive and can often cost several thousands of dollars per included candidate (e.g., above $6,000 per included candidate), such that improperly including one, tens, hundreds, or more candidates quickly becomes a costly error.

In this regard, conventional data labeling methodologies, particularly in the context of difficult to diagnose diseases, often produces poor labels. For long-term risk prediction, for example diagnosing early symptoms of the difficult to diagnose disease, additional problems lead to data labelling with even worse accuracy. For example, slow disease progression is usually coupled with provider variation in recording disease onset and symptoms, which may lead to improperly labelling a candidate or difficulty in identifying a proper time associated with onset of the disease. As another example, patients do not always recognize their symptoms, and thus often do not bring them to the attention of a provider, or the health care system may not record all pertinent facts about a patient for a particular visit or set of visits to a provider. These problems further inhibit the ability to label data associated with such candidates.

Conventional machine learning applications utilizing a defined source of truth must have a definitive label to learn. To do so, conventional machine learning applications discard candidates that do not fall squarely into a defined label (e.g., a case or a control for a RCT or treatment). With difficult to diagnose diseases, for example, the number of candidates that do not fall into a defined label may embody a large portion of the population, or even a majority of the population. By using only a limited candidate pool and discarding a large portion of the population, such machine learning applications can limit accuracy of the model, or even bias their results based on the chosen truth source(s).

Conventionally, incorrect data labelling on example cases may lead to training a model to learn the inaccurate labeling method instead of an absolute truth. Traditionally, this is called the noisy label problem. Generally, this problem assumes that noisy (i.e., incorrect) labels occur at random and possibly with different error rates within each class. Conventional machine learning models may adapt when the noisy labels are random. For example, "Learning with Noisy Labels" by Natarajan et al., the content of which is incorporated by reference herein in its entirety, describes the problem of noisy labels and adaptations when noise is random. However, in some contexts, such as healthcare data analysis and diagnosis of difficult to diagnose diseases, incorrect labeling generally does not occur at random. For example, under-diagnosis occurs due to candidate age, health complexity, provider expertise (or lack thereof), transcription of medical data into claim systems, provider systems, and EHR systems. Inventors have identified the non-random nature of the errors on such labels as an opportunity to learn how and/or why generated labels are incorrect and to fix the improper label. While some conventional methodologies accept the labeling of patients from claims and EHR data, such labelling is ineffective for difficult to diagnose diseases that lack a conclusive test. Further, solutions that target the noisy labels (for example to address under-diagnosis) do not link the models to subsequent predictive models.

Inventors have established that noisy labelling is a significant issue that impedes the ability to make predictions of disease onset, for example as described in "Identifying Incident Dementia by Applying Machine Learning to a Very Large Administrative Claims Dataset" by Nori et al, the content of which is incorporated herein by reference in its entirety. In this regard, if disease diagnosis is incorrect, attributed to the wrong date of onset, altogether missing, or otherwise not well-labelled, making predictions based on the error-prone dataset using conventional machine learning model methodologies will also be error-prone. In this regard, such conventional methodologies are at risk of a conventional machine learning model learning how to mimic the errors in labeling rather than correctly determine the risk of disease onset for a particular target disease.

Embodiments of the present disclosure provide for data labelling according to a defined ruleset using a dual-prediction model system, improving accuracy of the generated data labels with respect to long-term predictions (e.g., predictions based on historical data from X years ago, where X is a number or a range of numbers) and enabling labelling of data associated with candidates that were previously discarded. In this regard, embodiments train and utilize a candidate label probabilistic model to generate a candidate positive-label probability associated with a corresponding label rather than generating the label itself. In the context of labelling candidates as a case or control for purposes of a RCT, the generated candidate positive-label probability represents a probability that the data associated with the candidate (e.g., electronic health records and/or claim data having particular features) indicates the candidate should be labeled a case, for example such that the probability indicates how much this candidates features match all other cases learned by the model. This probability score captures the degree of belief in the truth of the case label based on the data in hand, rather than relying purely on the label, which captures more information than a pure classification label of case or control. It should be understood that, in some embodiments, the generated probability may be associated with a control label instead of a case label.

The candidate label probabilistic model learns label probability generating to ensure that candidates with the same features represented within their corresponding data records have the same probability of receiving a particular label (e.g., same probability of being labeled a case). In the context of labeling candidates for an RCT into a case cohort or a control cohort, for example, this means that candidates with the medical features are scored to have the same probability of having a case label assigned. The data records may be any structured and/or unstructured medical data (e.g., CPT, HCPCS, ICD, RX claim, and EHR data) collected for a particular period, for example just before a date of diagnosis or other critical date (e.g., an index date). The engineered facts can be encoded and/or otherwise embedded into a vector space. The model can then be fit with a suitable classifier to fit the value of probability of a label given the features represented by the data, for example represented by probability(case|feature).

Additionally or alternatively, in some embodiments, upon training and/or fitting the candidate label probabilistic model, the trained candidate label probabilistic model is further adjusted to better reflect the true population based probabilities. For example, in some circumstances, to ensure the model fitted values are in fact the appropriate probabilities, the embodiments are adjusted based on the ideas of King, Gary, and Langche Zeng. "Logistic Regression in Rare Events Data." Political Analysis, vol. 9, no. 2, 2001, pp.

137-63. DOI.org (Crossref), doi:10.1093/oxfordjournals.pan.a004868 [https://gking.harvard.edu/files/Os.pdf] the contents of which are incorporated by reference herein in its entirety, regarding predicting rare social events. In this regard, the training data utilized to train the candidate label probabilistic model rarely matches the real-world population prevalence of positive and/or negative candidates (e.g., candidates with medical data indicating a "case" label should be assigned, and candidates with medical data indicating a "control" label should be assigned). In this regard, the apparatus 200 is configured to adjust the candidate label probabilistic model during training, to fit the trained candidate label probabilistic model for generating candidate positive-label probabilities that truly reflect corresponding real-world probabilities of the candidate being associated with a particular label (e.g., a "case" label indicating diagnosis of a particular disease").

The candidate label probabilistic model may be embodied in any of a myriad of machine learning implementations, for example, logistic regression to determine a probability of the candidate being assigned a certain label, another maximum-likelihood estimator to determine a probability of the candidate being assigned a certain label, a deep learning implementation to determine a probability of the candidate being assigned a certain label by creating a neighborhood of probabilities around a certain candidate positive-label probability and generating an adjusted candidate positive-label probability based on the neighborhood (e.g., by taking the ratio of the positive score neighborhood count indicating a target label to the total score neighborhood count or updated total score neighborhood count), a clustering implementation to determine a probability of the candidate being assigned a certain label based on a ratio of a cluster positive score count (e.g., representing the number of candidate positive-label probabilities in the cluster that are associated with the desired label) to the total cluster count (e.g., representing a cluster size), and/or the like, or a combination thereof.

While some such implementations may generate well-calibrated probabilities, other model implementations (for example some clustering and/or deep learning implementations) may require post-processing to adjust the probability to represent a well-calibrated probability. Some embodiments utilize a score adjustment range to adjust a generated probability to reflect a well-calibrated probability. For example, the score adjustment range functions as a caliper for creating a neighborhood of candidates around a particular probability generated for a particular candidate. The neighborhood may comprise the other probabilities within a candidate positive-label probability set for other candidates, which may comprise a certain number of positive score count (e.g., candidates corresponding to a generated candidate positive-label probability that reflects a case) and a total neighborhood count (e.g., all generated candidate positive-label probabilities). If the total neighborhood count does not satisfy a particular threshold, the score adjustment range may be increased by a particular score adjustment factor (e.g., doubled, tripled, or multiplied by any other scaling factor) to create a larger neighborhood to attempt to encompass more candidate positive-label probabilities. Embodiments may continue to adjust the score adjustment range based on the score adjustment factor, for example until the total score neighborhood count satisfies the neighborhood count threshold. When a satisfactory neighborhood has been determined, the candidate positive-label probability may be adjusted based on the positive score neighborhood count and the updated total neighborhood count. For example, in some embodiments, the adjusted candidate positive-label probability is generated by taking the ratio of the positive score neighborhood count (e.g., the number of positive-label score probabilities indicating a case label) to the total score neighborhood count or updated total score neighborhood count. In some such embodiments, the neighborhood count threshold is pre-determined and/or generated based on at least a desired certainty level and/or other factors. In some embodiments, the neighborhood count threshold and/or one or more post-processing algorithms are performed to enforce monotonicity of the adjusted candidate positive-label probabilities. Embodiments utilizing such adjusted candidate positive-label probabilities may provide a further boost to overall model performance. It should be appreciated that, additionally or alternatively, the neighborhood count threshold is determined and/or predetermined based on one or more of the machine learning model implementation, disease the model is linked to, and/or disease-related parameters such as disease rarity.

The candidate label probabilistic model provides a plurality of technical, business, and medical advantages over previous labelling models and methodologies. For example, whereas conventional labelling models would evaluate false positives and/or false negatives as errors, the candidate label probabilistic model described herein utilizes such cases. For example, in the context of medical diagnosis labeling, a false positive—meaning a candidate without a diagnosis of a disease but with a high candidate positive-label probability for the disease—may provide an example of an under-diagnosed candidate that is wrongly labelled. The high candidate positive-label probability is kept for the candidate, rather than thrown out as an error, and used to consistently label other candidates that share similar features based on their associated data records.

Similarly, candidates labelled as a case but associated with a low candidate positive-label probability indicates the candidate's data records do not share features of other candidates labelled as a case. In one example context, this candidate may have visited a hospital and was diagnosed with a disease without a symptomatic history present in the candidate's data records. The low candidate positive-label probability is kept for the candidate, rather than dismissing it as an error, and used to consistently label other candidates that share similar features based on their associated data records (or lack thereof). The candidate label probabilistic model is designed to discount these patients because their data records are not similar to those of the majority of candidates labelled as cases (or alternatively where the model is configured to predict the probability of being a control or another label, the data records are not similar to those of the majority of candidates labelled as controls). Such candidates may similarly be poor RCT candidates, for example because they have records within a particular timestamp interval representing the modeling window. In the context of medical diagnosis labeling, this may mean that the candidate is not an active participant in their own health care (e.g., does not often consult a healthcare provider) and thus is a poor RCT candidate.

The candidate label probabilistic model is designed to enable scoring of all candidates, rather than just confirmed candidates associated with a particular label (e.g., confirmed cases and/or controls). Conventionally, a ruleset is used to generate a positive candidate set that meet all rules in the ruleset (e.g., confirmed cases) and a negative candidate set that meet none of the rules in the ruleset (e.g., confirmed controls). In conventional implementations, all remaining candidates that have met at least one rule but not all rules form a neutral candidate set that is considered unconfirmed, and this neutral candidate set is thrown out for purposes of consideration for both training and labeling. The candidate label probabilistic model instead removes the neutral candidate set for training purposes, but can then be scored to determine a corresponding candidate positive-label probability for each candidate in the neutral candidate set. These candidates can then be used in subsequent steps, such as a long-term prediction step, which improves the predictive power of the model, increases the potential size of the case and/or control (or other label) cohorts.

Embodiments of the disclosure build on these advantages by utilizing a second model for long-term historical prediction based on the probabilities, i.e., the candidate positive-label probability set, generated by the candidate label probabilistic model. A historical record prediction model labels candidates based on data records within a second timestamp interval, for example based on data records that predate the index date for each candidate by a certain length of time (e.g., 5-10 years before the index date for a candidate) and that predate the modeling window for the candidate label probabilistic model (e.g., up to 2 years before the index date for the candidate). Embodiments utilize the predicted labels instead of the original labels for each candidate (e.g., generated based on the ruleset), which can be used to fit the historical record prediction model to generate the labels based on the earlier, long-term historical data set for each candidate. In this regard, fitting the historical record prediction model creates and/or enables a number of independent prediction models, one for each year from the index date of the candidate for the second modeling window embodied within the long-term historical data set (e.g., for 5-10 years from the index date for the candidate, a prediction model for 5-, 6-, 7-, 8-, 9-, and 10-years from the index date).

The historical record prediction model can lead to various improvements in prediction accuracy, consistency, and robustness. Further, the historical record prediction model is configured to score unconfirmed candidates (e.g., candidates assigned to a neutral candidate set), thus increasing the overall candidate pool size produced by the final prediction step. In this regard, at least one of the technical advantages provided by embodiments herein with respect to the historical record prediction model are built on advantages provided by the specific implementations of the candidate label probabilistic model described herein.

Embodiments of the present disclosure are particularly advantageous in example contexts of patient recruitment for preventative and therapeutic clinical trials, and identification of patients for prevention of disease or medical intervention, for difficult to diagnose diseases. For example, as many as 35.6 million people worldwide lived with dementia in 2010, which is expected to double every 20 years, with cases in the United States more than doubling in the same timeframe. Coupled with this increase is a significant rise in total expected health care and long-term care costs, which have already reached a historical high in 2017. These problems emphasize the significant need to improve treatment options for patients with early stage dementia. Improving candidate selection for RCTs, treatment, or the like, may lead to decreased failures of RCTs, improved identification of treatment effectiveness, or the like.

Inventors have identified that, utilizing the embodiments described herein improvements in label prediction accuracy are achievable. For example, using dementia diagnosis as an example, significant improvements in accuracy may be achieved for 5-10 years from the index date. For example, Table 1 provides example improvement data according to test implementations of embodiments:

TABLE 1

Improvements of Embodiments of the Present Disclosure Compared to Conventional Baseline Models

| Dementia Models 10 years out | Prevalence | AUC | Sensitivity | Specificity | F1 |
| --- | --- | --- | --- | --- | --- |
| Conventional Baseline | 6.7% | 62.9% | 16.4% | 92.8% | 0.15 |
| Embodiments with Learned Labels (only original cases/controls) | 6.7% | 70.2% | 21.4% | 93.5% | 0.20 |
| Embodiments with Learned Calibrated label | 6.7% | 70.8% | 23.3% | 93.2% | 0.21 |

Definitions

In some embodiments, some of the operations above may be modified or further amplified. Furthermore, in some embodiments, additional optional operations may be included. Modifications, amplifications, or additions to the operations above may be performed in any order and in any combination.

Many modifications and other embodiments of the disclosure set forth herein will come to mind to one skilled in the art to which these inventions pertain having the benefit of the teachings presented in the foregoing description and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

As used herein, the terms "data," "content," "digital content," "digital content object," "information," and similar terms may be used interchangeably to refer to data capable of being transmitted, received, and/or stored in accordance with embodiments of the present disclosure. Thus, use of any such terms should not be taken to limit the spirit and scope of embodiments of the present disclosure. Further, where a computing device is described herein to receive data from another computing device, it will be appreciated that the data may be received directly from another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to another computing device or may be sent indirectly via one or more intermediary computing devices, such as, for example, one or more servers, relays, routers, network access points, base stations, hosts, and/or the like.

The term "positive candidate" refers to a candidate determined to satisfy all rules of a particular ruleset. In this regard, a positive candidate is confirmed associated with a provisional first label corresponding to satisfying all rules of a particular ruleset. In some embodiments, in the context of medical diagnosis for purposes of RCT candidates, a positive candidate is confirmed as labeled a case based on meeting a ruleset for diagnosing a particular disease.

The term "negative candidate" refers to a candidate determined to none of the rules of a particular ruleset. In this regard, a negative candidate is confirmed associated with a provisional second label corresponding to satisfying none of the rules of a particular ruleset. In some embodiments, in the context of medical diagnosis for purposes of RCT candidates, a negative candidate is confirmed as labeled a control based on meeting none of the rules in a ruleset for diagnosing a particular disease.

The term "neutral candidate" refers to a candidate determined to satisfy at least one rule of a particular ruleset, but not all rules of the particular ruleset. In this regard, a neutral candidate is unconfirmed and associated with provisional label corresponding to satisfying some but not all the rules of a particular ruleset. In some embodiments, in the context of medical diagnosis for purposes of RCT candidates, a neutral candidate is unconfirmed and labeled as unconfirmed based on meeting some but not all of the rules in a ruleset for diagnosing a particular disease.

The terms "index" and "index date" refer to electronically managed timestamp data representing a critical date where a candidate is associated with a label based on the data records for the candidate, such that the index date may be used as a starting point for retrospective processing of the data over one or more timestamp intervals. For example, in the context of medical diagnosis labeling, the index date represents a timestamp representing a date that data records corresponding to a particular candidate indicate the candidate should be labelled a case (e.g., all rules are met of a ruleset for diagnosing a particular disease), such that the index date represents the timestamp with the earliest occurrence of the code. In some embodiments, an index date for a candidate is dependent on a determined preliminary label for the candidate. For example, in some embodiments, a positive candidate is associated with a most recent index date based on the latest data record utilized in determining a candidate satisfies all rules of a rule set. Additionally or alternatively, in some embodiments, a neutral candidate is associated with associated with a most recent index date based on the latest data record used in determining a candidate satisfies any rule of a rule set. Additionally or alternatively, in some embodiments, a negative candidate is associated with a pre-determined or randomized index date upon determining the candidate does not satisfy any rule of a corresponding rule set.

The term "candidate positive-label probability" refers to electronically managed data, generated by a candidate label probabilistic model, representing a probability that a candidate is associated with a particular label based on data records corresponding with the candidate within a first defined timestamp interval. In some embodiments, the candidate positive-label probability is represented as a percentage stored utilizing one or more data types (e.g., a float, a double, a string, or the like). In an example context, a candidate positive-label probability represents a probability that data records indicate the candidate should be associated with a "case" label, or a "control" label.

The term "historical candidate positive-label probability" refers to electronically managed data, generated by a historical record prediction model, representing a probability that a candidate is associated with a particular label based on data records corresponding with the candidate within a second defined timestamp interval, the second timestamp interval preceding a first timestamp interval utilized in generating a candidate positive-label probability. In some embodiments, the candidate positive-label probability is represented as a percentage stored utilizing one or more data types, for example a "case" label or a "control" label.

System Architecture and Example Apparatus

The methods, apparatuses, systems, and computer program products of the present disclosure may be embodied by any variety of devices. For example, a method, apparatus, system, and computer program product of an example embodiment may be embodied by a fixed computing device, such as a personal computer, computing server, computing workstation, or a combination thereof. Further, an example embodiment may be embodied by any of a variety of mobile terminals, mobile telephones, smartphones, laptop computers, tablet computers, or any combination of the aforementioned devices.

In this regard, FIG. 1 discloses an example computing system in which embodiments of the present disclosure may operate. FIG. 1 illustrates an overview for a system configured for data labelling according to a defined ruleset using a dual-prediction model system. Specifically, the system includes a client device for communicating with one or more systems, for example a label prediction system 102, configured for predicting and/or assigning one or more labels for a candidate. Additionally or alternatively, the label prediction system 102 is further configured to provide various data analysis and/or processing functionality. For example, in an example context, the label prediction system 102 is embodies, or is a sub-system of, a healthcare data analysis and processing system.

Specifically, as illustrated, the system includes a label prediction system 102. The label prediction system 102 comprises a label prediction server 102A ("server 102A") and a label prediction datastore 102B ("datastore 102B"). The server 102A and/or datastore 102B may be hardware, software, firmware, or a combination thereof, specially configured to provide the functionality described herein. In this regard, the server 102A may be configured to communicate with the datastore 102B, via one or more local and/or remote communications networks to enable the label prediction system to provide such functionality described herein.

The server 102A may be embodied by a computer or a plurality of computers. The server 102A may provide various functionality associated with receiving requests, for example from one or more client devices, for processing and/or analyzing one or more data records, processing such data records, and/or providing data based on or generated in response to such processing to one or more client devices associated with the request, for example client device 104. For example, in some embodiments the server 102A is configured to generate one or more probabilities for associating with a candidate based on one or more data records. In some such embodiments, the server 102A is configured to communicate with one or more external datastores, additionally or alternatively to the datastore 102B, to generate one or more probabilities for assigning a corresponding label to one or more candidates. For example, the server 102A may generate probabilities and/or labels for transmitting to the client device 104, for example automatically or in response to one or more user requests. The server 102A may access the communications network 108, and/or one or more alternative networks or sub-networks therein, to perform one or more of the operations described herein.

The datastore 102B may be embodied as a data storage device, such as one or more local storage device(s), one or more cloud storage device(s), network attached storage ("NAS") device or a plurality of NAS devices, or as a separate database server of plurality of servers. The datastore 102B includes information accessed by, receive by, and/or otherwise generated and/or processed by the server 102A to facilitate operations provided by the label prediction system 102. For example, the datastore 102B may be configured to store, without limitation, a plurality of data records associated with one or more candidate identifiers, one or more user account details corresponding to user accounts permissioned to access the label prediction system 102, one or more software applications, executables, instructions, codes, and/or the like, or any combination thereof. Additionally or alternatively, the datastore 102B may be configured to store generated probabilities for one or more candidates and/or corresponding label designations based on generated probabilities.

The client device 104 may be embodied by any of a variety of computing devices as defined above. The client device 104 is configured to communicate with the label prediction system 102, for example via connectivity with the server 102A over communications network 108. Electronic data received by the server 102A from the client device 104 may be provided in various forms and via various methods for processing. For example, the client device 104 may include desktop computers, laptop computers, smartphones, netbooks, tablet computers, wearables, and/or the like. The client device 104 may include a networking interface to enable such communications, and/or client device 104 may include, or be associated with, a device or component configured as a network interface to enable such communications (e.g., a wearable device connected to a smartphone). The client device 104 may be configured to enable communications over various networks utilizing various networking hardware, software, and/or firmware (e.g., Bluetooth between a smartphone and associated wearable, a carrier network between a smartphone and the label prediction system 102 and/or between a wearable and the label prediction system 102, and/or one or more wireless and/or wireless networks for communicating via the Internet between a client device and a label prediction system 102).

In an example context, the client device 104 may execute an application or "app" to enable interaction with the label prediction system 102. Such applications are typically designed for execution via a computing device dependent on the operating system and/or other configurations associated with the computing device. For example, an application may be provided that executes on mobile device operating systems such as iOS®, Android®, or Windows®. Alternatively, an application may be provided that executes on a personal computer operating system, such as Windows®, macOS®, Linux®, or another operating system executed on a laptop device, desktop device, or terminal device. These platforms typically provide frameworks that allow applications to communicate with one another and/or with particular hardware and/or software components of the client device. For example, the mobile operating systems and/or personal computer operating systems named above each provide frameworks for interacting with location services circuitry, wired and/or wireless network interfaces, user contacts, and other applications. In an example context, the application is embodied by a service application provided by the label prediction system or an associated system. Communication with hardware and software modules outside of the application is typically provided via one or more application programming interfaces (APIs) configured by the operating system for the client device.

Alternatively or additionally, the client device 104 may interact with label prediction system 102 via a web application. In an example context, the web application is embodied by a web browser executed via the client device 104. As yet another example, the client device 104 may include various hardware, firmware, and/or software designed to interface with the label prediction system 102.

The external datastore 106 may represent an external system, resource, service, datastore, computer, software application, and/or the like, that is accessible by a label prediction system 102 for processing. In some embodiments, the external datastore 106 is configured to maintain one or more candidate data records corresponding to one or more candidate users. In an example context, the external datastore 106 is configured to store data records associated with healthcare related services, treatment, and/or the like, such as EHR data records. For example, the external datastore 106 embodies a healthcare provider system, hospital system, third-party records datastore system, and/or a combination thereof. In some embodiments, the external datastore 106 embodies one of a plurality of external datastores communicable with the label prediction system 102. For example, the label prediction system 102 may be configured to retrieve data records embodying candidate data from any number of local, remote, and/or cloud data storages associated with any number of entities. In some embodiments, the external datastore 106 is communicable via one or more APIs. The label prediction system 102 may be configured to communicate with the external datastore 106 via transmissions over the communications network 108 (e.g., over one or more wireless and/or wired Internet connections).

Example Apparatuses of the Disclosure

Having described an example system according to the scope of the present disclosure. The label prediction system 102 may be embodied by one or more computing systems, devices, and/or apparatuses, such as the apparatus 200 shown in FIG. 2. The apparatus 200 includes a processor 202, memory 204, input/output module 206, communications module 208, and label prediction module 210. The apparatus 200 may be configured, using one or more modules to execute the operations described herein.

Although the components are described with respect to functional limitations, it should be understood that the particular implementations necessarily include the use of particular hardware. It should also be understood that certain of the components described herein may include similar or common hardware. For example, two modules may both leverage use of the same processor, network interface, storage medium, or the like to perform their associated functions, such that duplicate hardware is not required for each module. The use of the term "module" and/or the term "circuitry" as used herein with respect to components of the apparatus 200 should therefore be understood to include particular hardware configured to perform the functions associated with the particular module as described herein.

Additionally or alternatively, the terms "module" and "circuitry" should be understood broadly to include hardware and, in some embodiments, software and/or firmware for configuring the hardware. For example, in some embodiments, "module" and "circuitry" may include processing circuitry, storage media, network interfaces, input/output devices, and the like. In some embodiments, other elements of the apparatus 200 may provide or supplement the functionality of the particular module. For example, the processor 202 may provide processing functionality, the memory 204 may provide storage functionality, the communications module 208 may provide network interface functionality, and the like, to one or more of the other modules.

In some embodiments, the processor 202 (and/or co-processor or any other processing circuitry assisting or otherwise associated with the processor) may be in communication with the memory 204 via a bus for passing information among components of the apparatus. The memory 204 may be non-transitory and may include, for example, one or more volatile and/or non-volatile memories. In other words, for example, the memory may be an electronic storage device (e.g., a computer readable storage medium). The memory 204 may be configured to store information, data, content, applications, instructions, or the like, for enabling the apparatus 200 to carry out various functions in accordance with example embodiments of the present disclosure.

The processor 202 may be embodied in any one of a myriad of ways and may, for example, include one or more processing devices configured to perform independently. Additionally or alternatively, the processor 202 may include one or more processors configured in tandem via a bus to enable independent execution of instructions, pipelining, and/or multithreading. The use of the terms "processor," "processing module," and "processing circuitry" may be understood to include a single-core processor, a multi-core processor, multiple processors internal to the apparatus, and/or remote or "cloud" processors.

In an example embodiment, the processor 202 may be configured to execute computer-coded instructions stored in the memory 204 or otherwise accessible to the processor. Alternatively, or additionally, the processor 202 may be configured to execute hard-coded functionality. As such, whether configured by hardware or software means, or by a combination thereof, the processor 202 may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

As one example context, the processor 202 may be configured to retrieve, receive, and/or identify candidate data records associated with one or more candidate identifiers. Additionally or alternatively, in some embodiments, the processor 202 embodies and/or configured to train, maintain, and/or utilize a candidate label probabilistic model and/or historical record prediction model. In this regard, the processor 202 is configured to process candidate data for generating one or more probabilities for labeling a candidate. Additionally or alternatively, in some embodiments, the processor 202 is configured to process a generated probability, such as a candidate positive-label probability and/or historical candidate positive-label probability, to associate the probability with a particular candidate label (e.g., a "case" label or "control" label). In some embodiments, the processor 202 is configured to perform one or more operations associated with such processing in response to requests received from a client device, for example a client device 104 (as illustrated in FIG. 1).

In some embodiments, the apparatus 200 may include input/output module 206 that may, in turn, be in communication with processor 202 to provide output to the user and, in some embodiments, to receive an indication of a user input (e.g., user interaction data). The input/output module 206 may comprise a user interface and may include a display to which the user interface is rendered. In some embodiments, the input/output module 206 may comprise a web user interface, a mobile application (e.g., a native mobile application or web application), a desktop application (e.g., a native desktop application or web application), a linked or networked client device, a kiosk, or the like. In some embodiments, the input/output module 206 may also include a keyboard, a mouse, a joystick, a touch screen, touch areas, soft keys, a microphone, a speaker, or other input/output mechanisms, peripherals, or the like. The processor and/or user interface module 206 comprising a processor, for example processor 202, may be configured to control one or more functions of one or more user interface elements through computer program instructions (e.g., software and/or firmware) stored on a memory accessible to the processor (e.g., memory 204, and/or the like).

The communications module 208 may be any means such as a device or circuitry embodied in either hardware or a combination of hardware and software that is configured to receive and/or transmit data from/to a network and/or any other device, circuitry, or module in communication with the apparatus 200. In this regard, the communications module 208 may include, for example, at least a network interface for enabling communications with a wired or wireless communication network. For example, the communications module 208 may include one or more network interface cards, antennas, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). In some such embodiments, the communications module 208 functions as a networking connection for facilitating communications between the apparatus 200 and one or more networked devices, such as a client device and/or one or more external datastore(s).

The label prediction module 210 includes hardware, software, firmware, and/or a combination thereof, configured to support functionality associated with label prediction system 102. The label prediction module 210 may utilize processing circuitry, such as the processor 202, to perform these actions. In some embodiments, the label prediction module 210 includes hardware, software, firmware, or a combination thereof, to receive, retrieve, and/or identify candidate data for processing. Additionally or alternatively, in some embodiments, the label prediction module 210 includes hardware, software, firmware, or a combination thereof, to process candidate data and generating one or more associated probabilities. For example, the label prediction module 210 is configured to train, maintain, and/or utilize a candidate label probabilistic model, Additionally or alternatively, the label prediction module is configured to train, maintain, and/or utilize a historical record prediction model. In some embodiments, the label prediction module 210 is further configured to analyze generated probabilities to associate the probabilities with a candidate label (for example, based on one or more predetermined rules and/or threshold (e.g., above a specific probability threshold the probability corresponds to a positive label such as a "case" label, and below the probability corresponds to a negative label such as a "control" label). It should be appreciated that, in some embodiments, the group-based communication module 210 may include a separate processor, specially configured field programmable gate array (FPGA), or a specially configured application-specific integrated circuit (ASIC).

In some embodiments, one or more of the aforementioned components is combined to form a single module. For example, in some embodiments, the label prediction module 210 is combined with one or more other components, such as processor 202, into a single module. The combined module may be configured to perform some or all of the functionality described above with respect to the individual modules. Additionally or alternatively, in some embodiments, one or more of the modules described above may be configured to perform one or more of the actions described with respect to one or more of the other modules.

As described above, and as will be appreciated based on this disclosure, embodiments of the present disclosure may be configured as methods, mobile devices, frontend graphical user interfaces, backend network devices, and the like. Accordingly, embodiments may comprise various means including entirely hardware, entirely software, or a combination of hardware and software. Furthermore, embodiments may take the form of a computer program product on at least one non-transitory computer-readable storage medium having computer-readable program instructions (e.g., computer software) embodied in the storage medium. Similarly, embodiments may take the form of computer program code stored on at least one non-transitory computer-readable storage medium. Any suitable computer-readable storage medium may be utilized including non-transitory hard disks, CD-ROMs, flash memory, optical storage devices, or magnetic storage devices.

As will be appreciated, any such computer program instructions and/or other type of code may be loaded onto a computer, processor or other programmable apparatus circuitry to produce a machine, such that the computer, processor, or other programmable circuitry that execute the code on the machine creates the means for implementing various functions, including those described herein.

The computing systems described herein can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page or parseable data representation) to a client device (e.g., for purposes of displaying information/data to and receiving user input from a user interacting with the client device). Information/data generated at the client device (e.g., a result of the user interaction) can be received from the client device at the server.

While this disclosure contains many specific implementation details, these should not be construed as limitations on the scope of this disclosure or of what may be claimed, but rather as description of features specific to particular embodiments of particular inventions. Certain features that are described herein in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results, unless described otherwise. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products. Any operational step shown in broken lines in one or more flow diagrams illustrated herein are optional for purposes of the depicted embodiment.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results, unless described otherwise. In certain implementations, multitasking and parallel processing may be advantageous.

Example Computing Environment and Data Flow

FIGS. 3A, 3B, and 4-7 illustrates an example computing environment and data flow associated with embodiments of the present disclosure. In this regard, the computing environment may embody a software environment maintained by a label prediction system 102, for example embodied by the apparatus 200. Additionally or alternatively in this regard, the label prediction system 102, for example embodied by the apparatus 200, may be configured to process the electronically maintained data as described within the illustrated computing environments.

Figure 3A:
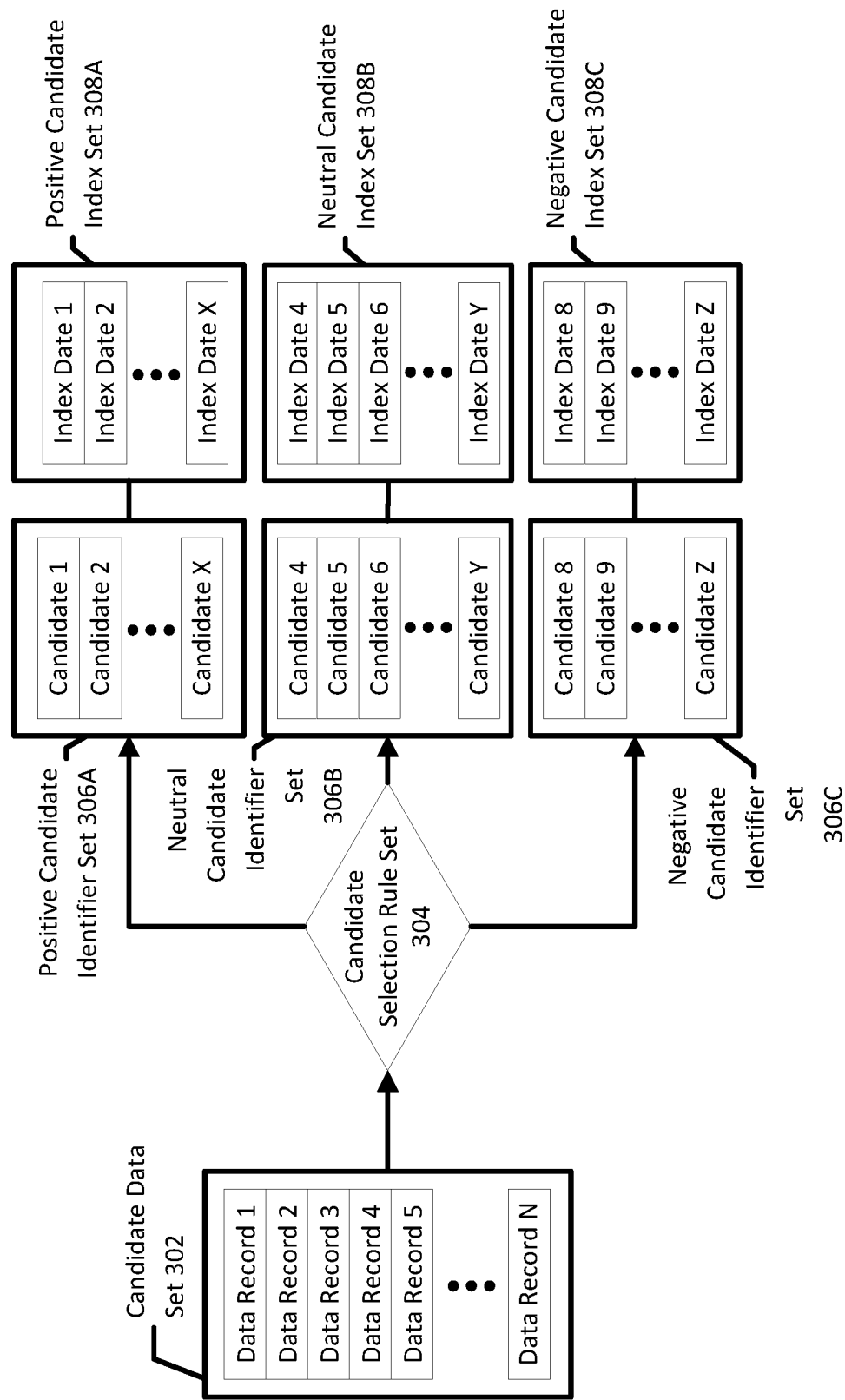

As illustrated in FIG. 3A, the apparatus 200 includes means, such as label prediction system 210, communications module 208, processor 202, and/or the like, or a combination thereof, to maintain candidate data set 302. The candidate data set 302 includes a plurality of data records associated with any number of candidates, for example one or more candidate(s) each associated with a candidate identifier. The candidate data set 302 may include data records maintained by the apparatus 200, or retrievable via communications with one or more external devices and/or systems, such as a client device and/or one or more external datastore(s). In an example context, each data record is associated with medical history for a particular candidate, including a candidate identifier, record date timestamp, content, and/or the like. Each record of the candidate data set may be embodied in any of a myriad of data formats, such as one or more data objects and/or associated data variables. A non-limiting example of a format for each data record in the candidate data set is illustrated and described below with respect to example data record 700.

In some embodiments, for example as illustrated, the apparatus 200 includes means, such as label prediction system 210, processor 202, and/or the like, or a combination thereof, to generate one or more corresponding candidate sets associated with one or more preliminary labels. In one example context, the apparatus 200 utilizes a candidate selection rule set 304 to generate one or more sets including identifiers for candidates that, based on the candidate selection rule set 304, are associated with a preliminary label (e.g., a "confirmed case" label, a "confirmed control" label, or an "unconfirmed" label). The apparatus 200 may utilize such means to retrieve the candidate selection rule set, for example from a local datastores and/or one or more remote systems and/or datastores, or the apparatus 200 candidate selection rule set 304 may be predefined, for example hard-coded into the system for usage. The candidate selection rule set 304 comprises one or more rules for analyzing candidate data record(s) associated with a particular candidate (e.g., a subset of the candidate data set 302 based on the candidate identifier linked for the candidate). In an example context of medical diagnosis labeling, the candidate selection rule set 304 embodies one or more computer-implemented rules for determining whether a data record subset for a particular candidate indicates the candidate should be indicated as diagnosed and/or should be diagnosed with a particular disease for purposes of assigning the candidate to a cohort for an RCT.

In this regard, the candidate selection rule set 304 may be utilized to split candidate identifiers associated with various candidates into one or more data sets for further processing. For example, the apparatus 200 may process the candidate data set 302 to assign preliminary labels separating the candidate identifiers into a positive candidate identifier set 306A, a neutral candidate identifier set 306B, and a negative candidate identifier set 306C. In the example context of RCT candidates, for example, each candidate identifier set may be generated based on whether the data records corresponding to the candidate identifier satisfies none, some, or all rules of the candidate selection rule set 304. In this regard, the apparatus 200 is configured to, for each candidate identifier associated with a data record in the candidate data set 302 (e.g., embodying a candidate pool identifier set), identify a subset of the candidate data set 302 corresponding to the candidate identifier. For example, the apparatus 200 may query the candidate data set 302 for data records linked to and/or associated with the candidate identifier (e.g., data records matching the value of the particular candidate identifier in a "candidate identifier" data field.

In some such embodiments, the apparatus 200 is configured to process the subset of candidate data set 302 corresponding to the candidate identifier to include the candidate identifier in an appropriate data set. The apparatus 200 may identify and process the subset of candidate data set 302 for each candidate identifier, and add the candidate identifier to an appropriate data set based on the processing of the subset of candidate data records. In an example context, such as assigning candidates to data sets associated with confirmation of a disease diagnosis, the positive candidate identifier set 306A represents candidates confirmed as diagnosed with, or should be diagnosed with, the disease based on the corresponding subset of data records satisfying all rules embodied by the candidate selection rule set 304. Further in this example context, the negative candidate identifier set 306C represents candidates confirmed as not diagnosed with the disease based on the corresponding subset of data records satisfying none of the rules embodied in the candidate selection rule set 304. Further in this example context, the natural candidate identifier set 306B represents candidates unconfirmed as diagnosable with the disease based on the subset of data records satisfying at least one of the rules but not all the rules embodied in the candidate selection rule set 304. In this regard, the apparatus 200 may be configured to associate each data set with a particular preliminary label. For example, the apparatus 200 may associate an "unconfirmed" label with the neutral candidate identifier set 306B, a "confirmed diagnosed" or "confirmed case" label with the positive candidate identifier set 306A, and a "confirmed undiagnosed" or "confirmed control" label associated with the negative candidate identifier set 306C. For example, the rule set may be embodied by one or more of Healthcare Effectiveness Data and Information Set (HEDIS) measures and/or other known algorithms for use in identifying a first date, based on the data records, that a candidate is linked to the disease.

Additionally or alternatively, as illustrated, the apparatus 200 processes the candidate data subset 302 to generate and/or determine an index date for each candidate identifier. In some embodiments, the index date for each candidate identifier is generated and/or determined based on whether the candidate identifier is added to the positive candidate identifier set 306A, neutral candidate identifier set 306B, or negative candidate identifier set 306C. For example, in a circumstance where the apparatus 200 determines the data records associated with a particular candidate identifier satisfy all rules of the candidate selection rule set 304, the apparatus 200 may determine a most recent data record used to satisfy one of the rules in the candidate selection rule set 304, where the most recent data record is associated with a particular timestamp. The timestamp for the most recent data record may represent a most recent index date associated with the candidate identifier. The most recent index date for the candidate identifier may be added to data set linked to the positive candidate identifier set 306A, for example added to the positive candidate index set 308A associated with the candidate identifier. In some embodiments, the apparatus 200 is configured to ignore all data records that are utilized to confirm that the candidate satisfies all rules for purposes of generating the index date.

Additionally or alternatively, in a circumstance where the apparatus 200 determines the data records associated with a particular candidate identifier satisfy at least one rule but not all rules of the candidate selection rule set 304, the apparatus 200 may determine a most recent data record used to satisfy one of satisfied the rules in the candidate selection rule set 304, where the most recent data record is associated with a particular timestamp. The timestamp for the most recent data record may represent a most recent index date associated with the candidate identifier. The most recent index date for the candidate identifier may be added to data set linked to the neutral candidate identifier set 306B, for example added to the neutral candidate index set 308B associated with the candidate identifier.

Additionally or alternatively, in a circumstance where the apparatus 200 determines the data records associated with a particular candidate identifier satisfies none of the rules of the candidate selection rule set 304, the apparatus 200 may generate an index date associated with the candidate identifier. For example, the apparatus 200 may generate a randomized index date selected from a record timestamp associated with any of the data records associated with the candidate identifier. In other embodiments, the apparatus may identify a predetermined index date selected from the data records (e.g., a predetermined number of data records from the most recent data records). The randomized index date, or predetermined index date, for the candidate identifier may be added to data set linked to the negative candidate identifier set 306C, for example added to the negative candidate index set 308C associated with the candidate identifier. In some embodiments, the candidate identifiers and corresponding index dates are embodied in a single data set (e.g., a data set storing data objects having a candidate identifier and an index date).

In some embodiments, the index date for one or more candidate identifier is provided as input. For example, in some embodiments, the index date for one or more positive candidate identifiers and/or one or more negative candidate identifiers may be provided as input. Additionally or alternatively, in some embodiments, the index date for one or more neutral candidate identifiers may be provided as input. In yet some other embodiments, one or more index dates for one or more neutral candidate identifiers is identified based on the above rules determinations.

Figure 3B:
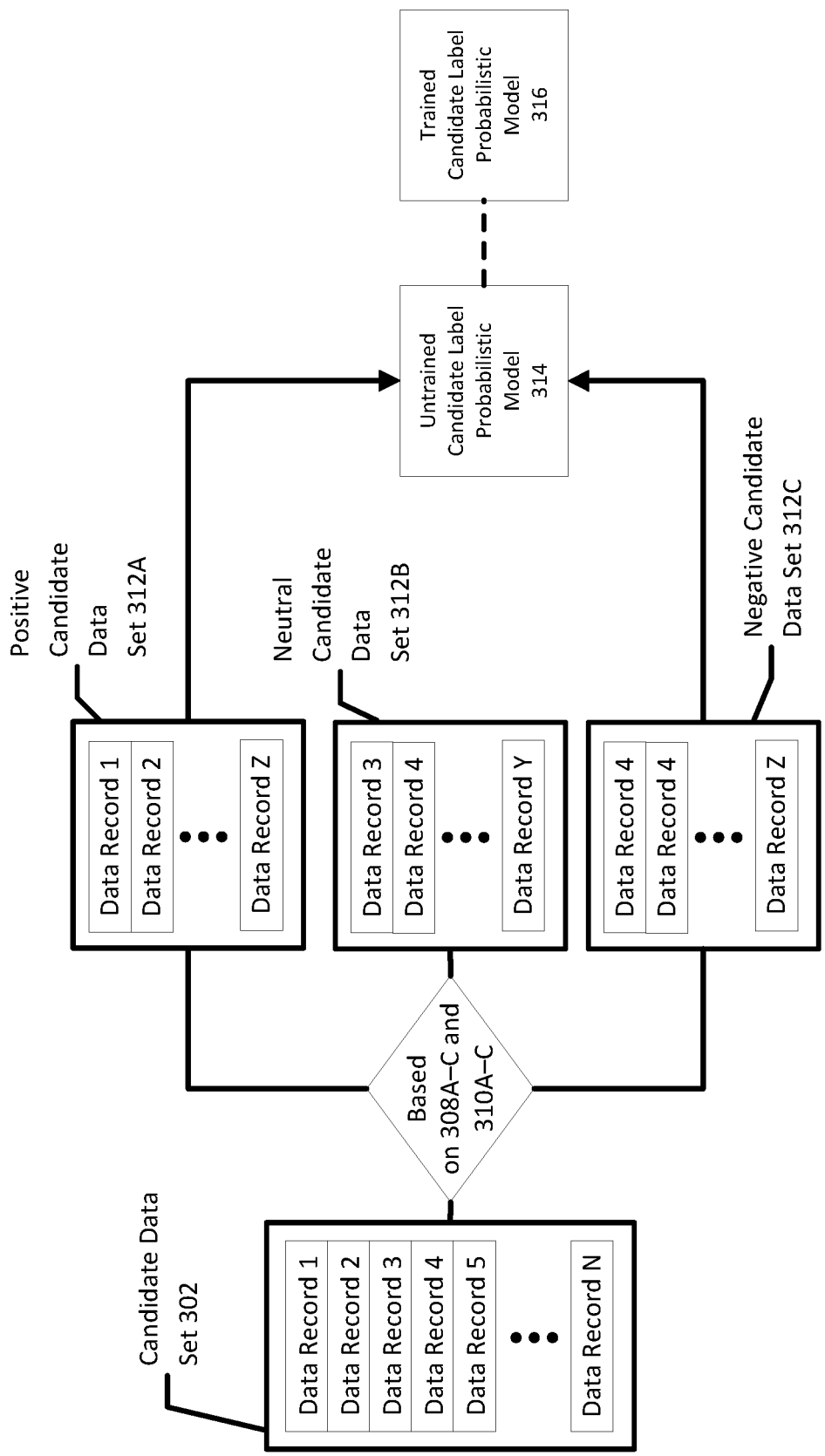

The apparatus 200 may continue to generate one or more predicted labels based as described with respect to the example computing environment and data flow illustrated with respect to FIG. 3B. As illustrated in FIG. 3B, the apparatus 200 includes means, such as label prediction system 210, communications module 208, processor 202, and/or the like, or a combination thereof, to identify one or more candidate data subsets from the candidate data set 302. Each of the candidate data subsets may be identified based on the candidate identifier sets 306A-306C and/or candidate index sets 308A-308C. For example, the apparatus 200 may identify the positive candidate data set 312A comprising the candidate data records of candidate data set 302 associated with candidate identifiers within the positive candidate identifier set 306A and before the index date of positive candidate index set 308A linked to each candidate identifier. Additionally or alternatively, the apparatus 200 may identify the neutral candidate data set 312B comprising the candidate data records of candidate data set 302 associated with the candidate identifiers within the neutral candidate identifier set 306B and before the index date of neutral candidate index set 308B linked to each candidate identifier. Additionally or alternatively, the apparatus 200 may identify the negative candidate data set 312C comprising the candidate data records of candidate data set 302 associated with the candidate identifiers within the negative candidate data set 306C and before the index date of negative candidate index set 308C linked to each candidate identifier.

In some embodiments, the apparatus 200 is configured to identify the candidate data subsets 312A-312C based on corresponding index dates and a particular timestamp interval. For example, for each candidate identifier, the subset of candidate data records may include data records associated with a record timestamp within a short-term record threshold of time before the index date. In the context of medical data records, for example, the apparatus 200 generates a candidate data subset for a given candidate identifier by identifying the records of candidate data set 302 that are associated with a services timestamp that falls between the index date and a determined historical threshold defining a specific timestamp interval (e.g., 2 years before the index date). In this regard, the candidate data record subset for each candidate identifier may be associated with various timestamp intervals. For example, the candidate data record subset for a first candidate identifier may include data records between a first corresponding index date (e.g., Mar. 1, 2012) and a determined historical threshold (e.g., 2 year interval—Mar. 1, 2010), while the candidate record subset for a second candidate identifier may include data records between a second corresponding index date (e.g., Jun. 19, 2015) and the determined historical threshold (e.g., 2 year interval—Jun. 19, 2013). It should be appreciated that, in other embodiments, the historical threshold may represent any desired timestamp interval, for example a prediction window input by a user via a corresponding client device. Alternatively, in some embodiments, the candidate data subsets 312A-312C includes all data associated with the corresponding candidate identifiers, which may be filtered and/or otherwise further split into subsets based on the index dates and/or one or more determined and/or predetermined thresholds. For example, in some embodiments, the positive candidate data set 312A includes all data records associated with candidate identifiers of the positive candidate identifier set 306A, and the apparatus 200 is configured to filter the positive candidate data set 312A based on the candidate positive candidate index set 308A to identify data records for purposes of training the untrained candidate label probabilistic model 314.

Additionally or alternatively, in some embodiments, the apparatus 200 is configured to maintain a candidate label probabilistic model for use in generating a positive candidate probability (e.g., a probability that a candidate identifier should be associated with a particular label, such as a "case" label). The apparatus 200 may utilize one or more subsets of the candidate data set 302 to train a candidate label probabilistic model for use in generating one or more candidate positive-label probabilities. For example, as illustrated, the apparatus 200 may generate, retrieve, and/or otherwise maintain an untrained candidate label probabilistic model 314. Further, in some embodiments, the apparatus 200 is configured to train and/or fit the untrained candidate label probabilistic model 314, converting the model and/or otherwise generating a corresponding trained model for use, for example the trained candidate label probabilistic model 316.

The apparatus 200 may train the untrained candidate label probabilistic model 314 utilizing one or more of the identifier subsets of candidate data set 302. For example, the apparatus 200 may train the untrained candidate label probabilistic model 314 utilizing a candidate label training subset of the candidate data set 302. In some embodiments, the candidate label training subset comprises all of the data records associated with the candidate identifiers of the positive candidate identifier set 306A and negative candidate identifier set 306C, or a subset thereof (e.g., before the index date and/or within a determined threshold interval). In an example context, the candidate label training subset comprises some or all of the positive candidate data set 312A and the negative candidate data set 312C. In this regard, the apparatus 200 is configured to train and/or fit the untrained candidate label probabilistic model 314 utilizing only confirmed candidates (e.g., in the context of RCT candidates, confirmed as diagnosed or confirmed as not diagnosed). Such embodiments do not utilize the neutral candidate data set 312B for training and/or fitting. In this regard, the trained candidate label probabilistic model 316 learns to generate probabilities that a candidate data records subset (for example, an index-limited candidate data set within a determined timestamp interval) associated with a candidate identifier indicates the candidate identifier is associated with a particular label (e.g., "case" label for diagnosis of a particular disease). Upon completing and/or fitting the candidate label probabilistic model, the apparatus 200 may be configured to maintain the trained candidate probabilistic model 316 for use.

It should be appreciated that, in training the untrained candidate label probabilistic model 314, only a subset of each data set (e.g., a subset of the positive candidate data set 312A and/or negative candidate data set 312C) may be used. In this regard, remaining data records not utilized for training may be utilized for model training validation and/or testing. In such embodiments, the apparatus 200 is configured to utilize known data set separation and/or partitioning for training, validation, and/or testing to ensure generation of a properly trained candidate label probabilistic model 316.

In some embodiments, the apparatus 200 is configured to utilize the candidate label training subset (e.g., comprising the positive candidate data set 312A and negative candidate data set 312C) to generate one or more candidate fact vectors to be used in training the untrained candidate label probabilistic model 314. In some such embodiments, a candidate fact vector includes data values for one or more data fields that represent whether certain facts and/or features are determined by the apparatus 200 to exist within the data records corresponding to the candidate identifier. In some embodiments, the candidate fact vector includes a data value representing one or more engineered features, for example counts over a particular timestamp interval (e.g., within 60 days) and/or total counts over a particular collection period. The apparatus 200 may be configured to, for each candidate identifier represented in the candidate label training subset, analyze one or more data records associated with the candidate identifier to determine values for one or more determinable facts, and store such values in a candidate fact vector associated with the candidate identifier. In this regard, the candidate fact vector may be utilized to train the untrained candidate label probabilistic model 314 to better predict the candidate positive-label probability corresponding to the preliminary label assigned to the candidate identifier (e.g., whether the candidate identifier was a positive candidate and associated with a "confirmed case" label, or the candidate identifier was a negative candidate and associated with a "confirmed control" label). In some such embodiments, the apparatus 200 is configured to train the untrained candidate label probabilistic model 314 utilizing demographic data for each candidate identifier. For example, demographic data values including, without limitation, age, race, height, weight, location, physical health indicators, and/or one or more derived values therefrom, are included as one or more factors in a candidate fact vector and/or used to generate a value for one or more candidate fact fields.

In some embodiments, for example, during model training the apparatus 200 is configured to match positive candidate identifiers and/or negative candidate identifiers based at least on a list of demographic and utilization facts indicated by the corresponding positive candidate data set 312A and/or negative candidate data set 312C. In this regard, matching such facts limits the model's exploitation of irrelevant correlations in the data. For example, the matching reduces confounding and improves prevalence of the corresponding probabilities for each label (e.g., in the RCT candidacy context, a "case" label or a "control" label) per stratum. For example, dementia is highly correlated to age, as are other conditions such as macular degeneration and keratosis, however age is not instructive on predicting dementia onset. In this regard, machine learning data may be matched by strata in a manner similarly described in Pearce, Neil. "Analysis of Matched Case-Control Studies." BMJ, February 2016, p. i969. DOI.org (Crossref), doi:10.1136/bmj.i969 [https://www.bmj.com/content/352/bmj.i969], the contents of which are incorporated by reference herein in its entirety. It should be appreciated that, in some such embodiments, training data may be matched (e.g., candidate identifiers and/or corresponding candidate data records of a positive candidate data set 312A and negative candidate data set 312C), but validation and/or test data remains unmodified to ensure validity of the validation or test.

Figure 4:
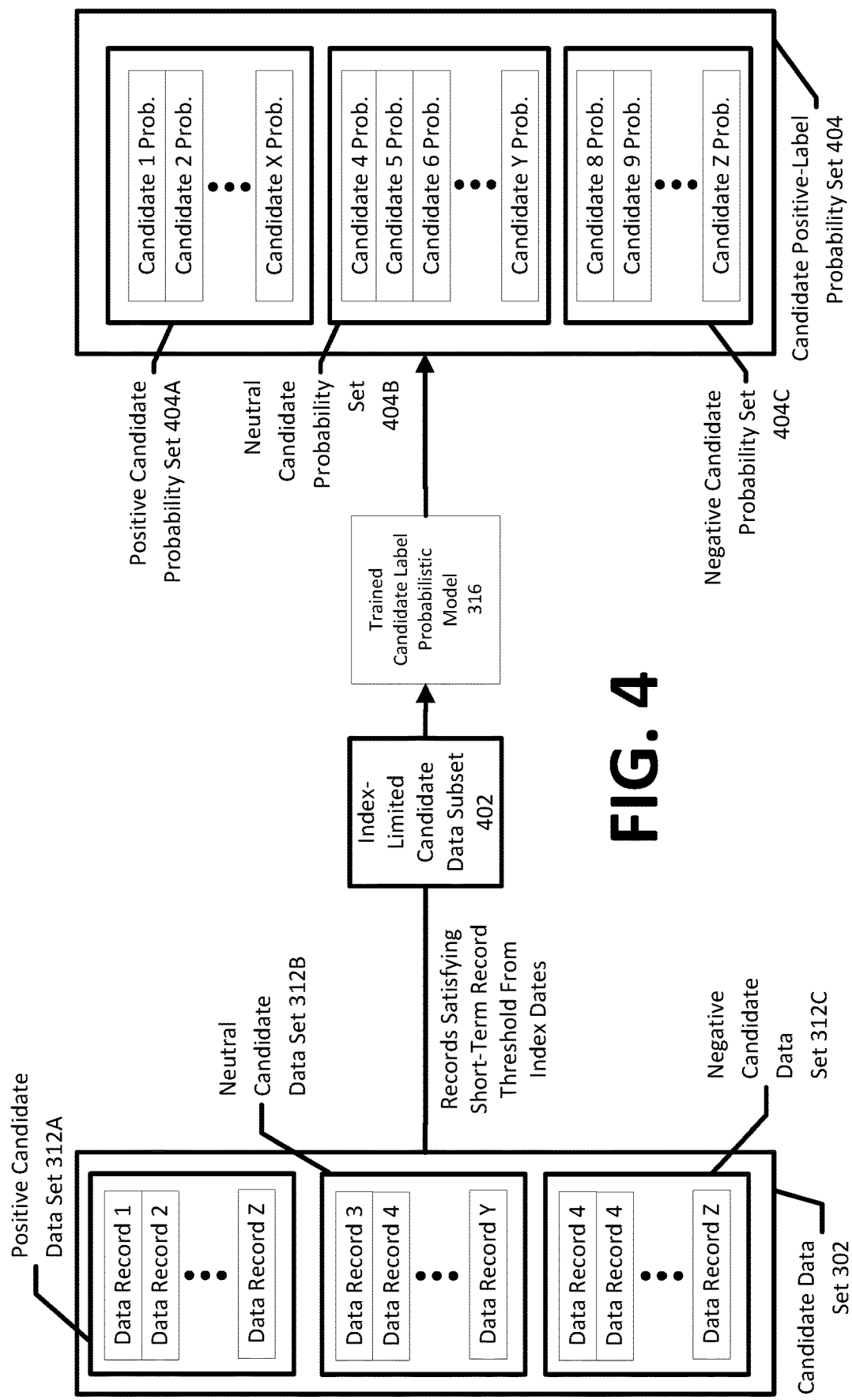

In some embodiments, the apparatus 200 is configured to generate one or more candidate positive-label probabilities (e.g., representing a probability of a particular label, for example associated with a disease diagnosis) as described with respect to the example computing environment and data flow illustrated with respect to FIG. 4. As illustrated in FIG. 4, the apparatus 200 includes means, such as label prediction system 210, communications module 208, processor 202, and/or the like, or a combination thereof, to apply one or more candidate data subset to the trained candidate label probabilistic model 316 to generate one or more corresponding positive candidate probabilities. In this regard, the apparatus 200 may be configured to generate a candidate positive-label probability set 404 that includes a candidate positive-label probability linked to each candidate identifier of a particular candidate pool identifier set. For example, the apparatus 200 may generate a candidate positive-label probability for each candidate identifier having at least a threshold number of records inn the candidate data set 302 (e.g., 1 or more records, X or more records where X is a number).

The trained candidate label probabilistic model 316 may be embodied using any of a number of machine learning implementations. For example, in some embodiments, the trained candidate label probabilistic model 316 is embodied by one or more logistic regression models and/or other maximum-likelihood estimator models to determine the probability that, based on the candidate data records for a particular candidate identifier, the candidate identifier should be assigned a particular label (e.g., the probability a candidate should be associated with a "case" label for a RCT). In other embodiments, the trained candidate label probabilistic model 316 is embodied by one or more deep learning models to determine the probability that, based on the candidate data records for a particular candidate identifier, the candidate identifier should be assigned a particular label. In some embodiments, the trained candidate label probabilistic model 316 generates an unadjusted probability that the apparatus 200 is configured to adjust to generate a calibrated candidate positive-label probability by identifying and processing a neighborhood of probabilities associated with the unadjusted candidate positive-label probability (e.g., a ratio of the number of positive candidates in a neighborhood to the total number of candidates in the neighborhood). In other embodiments, the trained candidate label probabilistic model 316 is embodied by one or more clustering models that cluster candidate identifiers, for example based on features identified in the candidate data records corresponding to a candidate identifier, and processing the cluster to generate a candidate positive-label probability (e.g., a ratio of number of positive candidates to cluster size). In this regard, in some embodiments, the trained candidate label probabilistic model 316 is configured to generate well-calibrated candidate positive-label probabilities. In other embodiments, the apparatus 200 is configured to perform one or more post-processing actions (e.g., neighborhood generation and processing) to generate a well-calibrated score from an unadjusted candidate positive-label probability.

As illustrated in FIG. 4, in some embodiments, the apparatus 200 is configured to identify an index-limited candidate data subset 402 from the candidate data set 302. In some embodiments, the index-limited candidate data subset 402 includes, for one or more candidate identifiers, corresponding candidate data records of the candidate data set 302 that satisfy a short-term record threshold from the index date for each of the candidate identifiers. In this regard, each data record of the index-limited candidate data subset associated with a particular candidate identifier may satisfy a short-term record threshold from the index date linked to the candidate identifier. In an example context, for a particular candidate identifier, the apparatus 200 identifies a predetermined short-term record threshold (e.g., two years for all candidate identifiers), identifies an index date for the candidate identifier (e.g., from one of the candidate index sets 308A-308C), and subsequently identifies all candidate data records on and/or before the index date and on and/or after a critical date adjusted from the index date using the predetermined short-term record threshold (e.g., two years before the index date). In this regard, each data record may include a data record timestamp associated with the data record (e.g., a services timestamp representing the date and/or time healthcare services were rendered). This process may be repeated for any number of candidate identifiers, such as for a candidate pool identifier set. In some embodiments, the apparatus 200 is configured to store the candidate data set 302 separately as positive candidate data set 312A, neutral candidate data set 312B, and negative candidate data set 312C utilizing the generated candidate identifier sets 306A-306C and/or candidate index sets 308A-308C to improve efficiency with searching the candidate data set 302 for records.

As illustrated, the apparatus 200 is configured to generate the candidate positive-label probability set 404, for example, by at least applying the index-limited candidate data subset 402 to the trained candidate label probabilistic model 316. The apparatus 200 may utilize the trained candidate label probabilistic model 316 to generate candidate positive-label probabilities for all candidate identifiers based on the index-limited candidate data subset 402 (or a subset other than the data records used for training), regardless of whether the candidate identifier was preliminarily associated with the positive candidate identifier set 306A (e.g., and thereby associated with a "confirmed case" label), the neutral candidate identifier set 306B (e.g., and thereby associated with an "unconfirmed" label), or the negative candidate identifier set 306C (e.g., and thereby associated with a "confirmed control" label). In this regard, the apparatus 200 is configured to produce candidate positive-label probabilities even for candidate identifiers not used in the training step (e.g., the neutral candidate identifier set 306B), and that was conventionally discarded entirely. For example, in some embodiments, the apparatus 200 is configured to generate a candidate positive-label probability for a candidate identifier, and add the generated the candidate positive-label probability linked to the candidate identifier in the candidate positive-label probability set 404 for storing.

In some embodiments, the apparatus 200 is configured to store the generated candidate positive-label probabilities within the same data structure and/or otherwise not separated, such that all candidate positive-label probabilities are retrievable within the same data object and/or sub-structure thereof. In some embodiments, the apparatus 200 is configured to store the generated candidate positive-label probabilities in any of a number of structured methodologies for improving storage and/or retrieval efficiencies. For example, in some embodiments, the apparatus 200 is configured to maintain a positive candidate probability set 404A, including candidate positive-label probabilities associated with each candidate identifier in the positive candidate identifier set 306A. Additionally or alternatively, in some embodiments, the apparatus 200 is configured to maintain a neutral candidate probability set 404B, including candidate positive-label probabilities associated with each candidate identifier in the neutral candidate identifier set 306B. Additionally or alternatively, in some embodiments, the apparatus 200 is configured to maintain a negative candidate probability set 404C, including candidate positive-label probabilities associated with each candidate identifier in the negative candidate identifier set 306C. In this regard, the apparatus 200 may further be configured to maintain parity between the candidate positive-label probabilities for a candidate identifier and a preliminary label associated with the candidate identifier.

Figure 5:
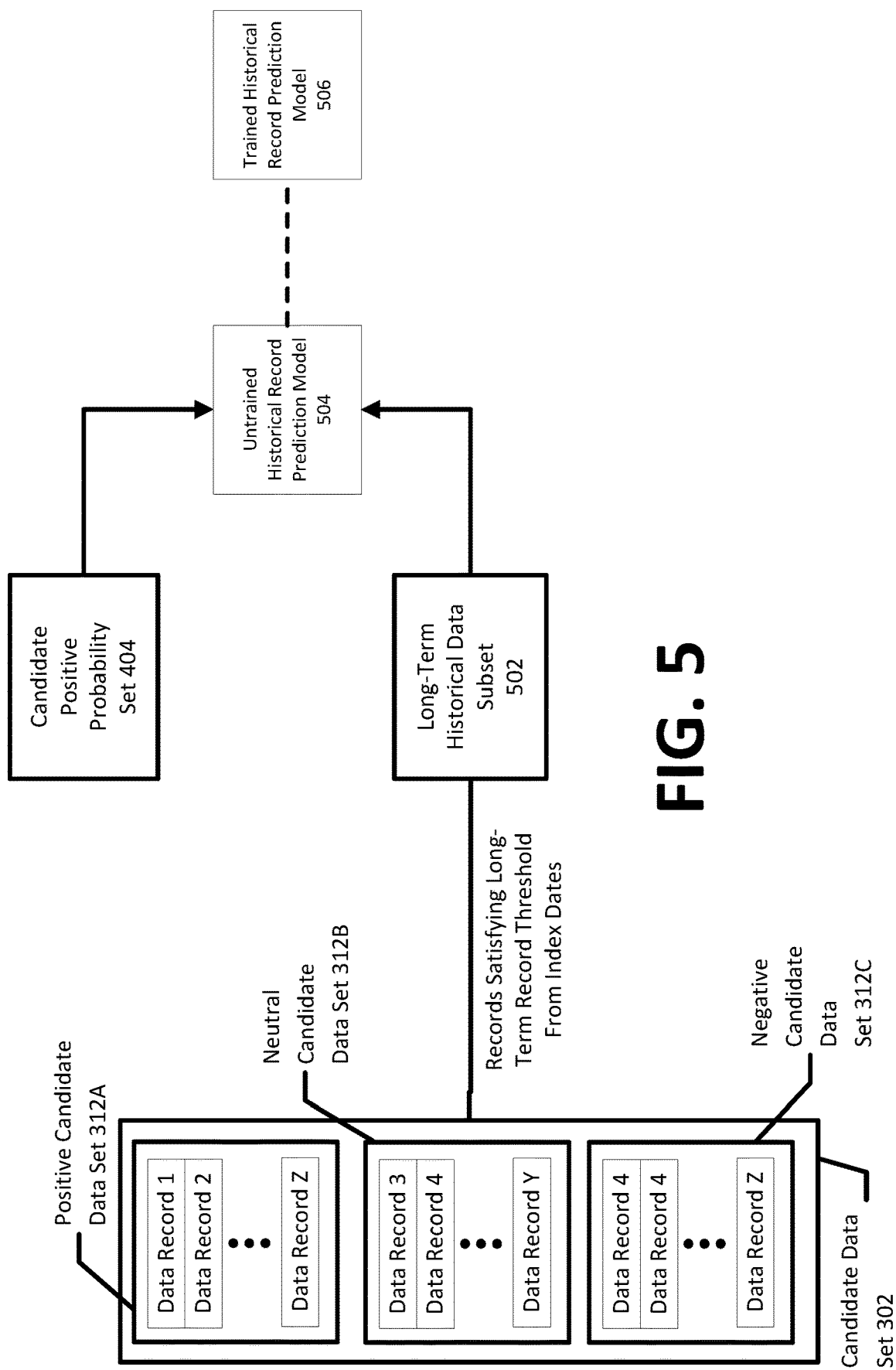

In some embodiments, the apparatus 200 is configured to train, fit, and/or otherwise maintain a historical record prediction model for use, as described with respect to the example computing environment and data flow illustrated with respect to FIG. 5. As illustrated in FIG. 5, the apparatus 200 includes means, such as label prediction system 210, communications module 208, processor 202, and/or the like, or a combination thereof, to identify, retrieve, and/or generate an untrained historical record prediction model 504. In some embodiments, the apparatus 200 is configured to generate the untrained historical record prediction model 504 upon execution. In other embodiments, the apparatus 200 receives the untrained historical record prediction model 504 from an associated system. It should be appreciated that the historical record prediction model may be embodied using any of a myriad of implementations, for example a logistic regression model, deep learning model, or the like.

Additionally or alternatively, in some embodiments, the apparatus 200 includes means, such as label prediction system 210, communications module 208, processor 202, and/or the like, or a combination thereof, to identify a long-term historical data subset 502 from the candidate data set 302 for use in training and/or fitting the untrained historical record prediction model 504. For example, in some embodiments, the long-term historical data subset 502 includes, for one or more candidate identifiers, corresponding data records of the candidate data set 302 that satisfy a long-term record threshold from the index date for each of the candidate identifiers. In this regard, each data record of the long-term historical data subset 502 may satisfy a long-term record threshold from the index date linked to the candidate identifier. In an example context, for a particular candidate identifier, the apparatus 200 identifiers a predetermined long-term record threshold (e.g., five years for all candidate identifiers), identifies an index date for the candidate identifier (e.g., from one of the candidate index sets 308A-308C), and subsequently identifies all candidate data records on and/or before the index date and/or after a critical date adjusted from the index date using the predetermined long-term record threshold (e.g., five years before the index date) and/or adjusted based on a short-term historical record threshold (e.g., between two years before the index date and seven years before the index date, such that the relevant timestamp intervals do not overlap). In this regard, each data record may include a data record timestamp associated with the data record (e.g., a service timestamp representing the date and/or time healthcare services were rendered). This process may similarly be repeated for any number of candidate identifiers, such as for the candidate pool identifier set.

The long-term historical data subset 502 and candidate positive-label probability set 404 may be utilized to train the untrained historical record prediction model 504. In this regard, the untrained historical record prediction model 504 may be trained, fit, and/or otherwise converted to the trained historical record prediction model 506. In this regard, the apparatus 200 utilizes the candidate positive-label probability set 404 and long-term historical data subset 502 to generate the trained historical record prediction model 506 that learned to predict the candidate positive-label probabilities of the candidate positive-label probability set 404 based on the corresponding data records of the long-term historical data subset 502. Advantageously, the trained historical record prediction model 506 is trained on the data sets for all candidate identifiers, and thus may be utilized for scoring a neutral candidate identifiers set, enabling access to a larger candidate pool set than conventional long-term prediction models. The trained historical record prediction model 506 is further advantageous over conventional models by being configured to predict the candidate positive-label probability set 404 rather than original labels. In this regard, whereas original labels associated with data records that are identical may differ, the trained candidate label probabilistic model 316 is configured to generate the same candidate positive-label probability for different candidate identifiers that have the same features identified in their corresponding data records.

Figure 6:
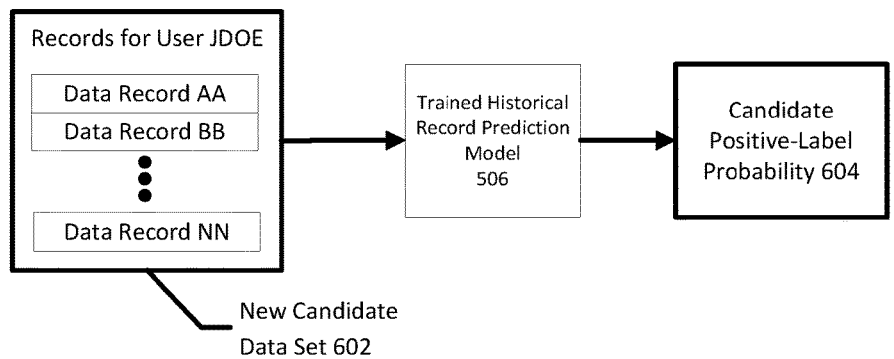

As illustrated in FIG. 6, in some embodiments, the apparatus is configured to enable use of a trained historical record prediction model 506 for generating a long-term candidate positive-label probability for one or more candidate identifiers. In some embodiments, the apparatus is configured to utilize the trained historical record prediction model 506 to generate a candidate positive-label probability for a new candidate. For example, the candidate identifier "JDOE" may be associated with candidate data set 602. The candidate data set 602 may include any number of data records having various data record types. In one such example context, the new candidate data set 602 includes one or more medical data records in structured and/or unstructured formats, including, without limitation, CPT claims, HCPCS claims, ICD claims, RX claims, EHR data records, or any combination thereof. Some or all of the new candidate data set 602 may be generated by the apparatus 200, received from an external system (e.g., an external datastore configured for storing medical records), and/or received from a client device.

The apparatus 200 may receive and/or retrieve the new candidate data set 602 and apply it to the trained historical record prediction model 506 to generate the candidate positive-label probability 604. In this regard, the candidate positive-label probability 604 represents the learned probability that the candidate identifier should be associated with a particular label (e.g., a "case" label in the context of RCT candidates) based on the new candidate data set 602. It should be appreciated that in some embodiments, the trained historical record prediction model 506 is configured to generate a probability between a lower bound and an upper bound (e.g., between 0 and 1, or between 0 and 100). In some embodiments, the apparatus 200 is further configured to process the candidate positive-label probability 604 to assign the candidate identifier a label and/or corresponding group. For example, in some embodiments, the apparatus 200 is configured to maintain a predetermined positive-label probability threshold and compare the candidate positive-label probability 604 to the predetermined positive-label probability threshold to determine whether the candidate positive-label probability satisfies the predetermined positive-label probability threshold for assigning an appropriate group. For example, in the example context of RCT candidacy, if the candidate positive-label probability 604 satisfies a predetermined positive-label probability threshold (e.g., is greater than or equal to the predetermined positive-label probability threshold), the candidate identifier is assigned the label of "case" and/or stored in a data set associated with candidates labelled as a "case." It should be appreciated that, in other embodiments, the apparatus 200 is configured to determine a positive-label probability threshold, for example such that a predetermined number or percentage of candidates satisfy the determined positive-label probability threshold.

FIG. 7 represents an example data object format of an example data record in accordance with example embodiments of the present disclosure. In this regard, it should be appreciated that, in some embodiments, the data record includes additional and/or alternative data fields. Alternatively or additionally still, in some embodiments, one or more data records is embodied by linked data fields (e.g., in one or more databases) not organized into a particular data object. In the context of medical record analysis, for example, a data record in the format or similar to the format of data record 700 may be created and/or stored to one or more datastores accessible to the apparatus 200 when a candidate visits a healthcare provider, hospital, and/or the like.

The data record 700 comprises a candidate identifier 702. The candidate identifier 702 may represent a numerical, alphanumeric, symbolic, alphabetical, or other data value that uniquely identifies a particular candidate. In this regard, it should be appreciated that a particular candidate may be associated with any number of data records based on the candidate identifier 702. For example, the apparatus 200 may query the value of candidate identifier 702 to determine the associated candidate. Similarly, the apparatus 200 may query the value of the candidate identifier field for a plurality of data records to generate a subset of related data records (e.g., data records all associated with the same candidate).

The data record 700 further comprises a record date timestamp 704. The record date timestamp may represent a string, numerical, date, or other data value representing a date and/or datetime associated with the data record 700. For example, in at least one example context, the record date timestamp 704 is assigned a value based on the date that the data record 700 is generated. Additionally or alternatively, in the example context of medical diagnosis labeling, the record date timestamp 704 may represent the date and/or datetime for the healthcare services performed and/or represented by the data record 700. In this regard, the apparatus 200 processes the value of the record date timestamp 704 to determine a date associated with the data record 700, for example to determine whether the date associated with the data record satisfies a short-term record threshold and/or a long-term record threshold.

The data record 700 further comprises record content 706. The record content 706 may include one or more data values representing content summarized by the data record 700. In the example context of medical data records, record content 706 may include one or more data values associated with services rendered to the candidate identified by candidate identifier 702 on the date identified by record date timestamp 704. For example, as illustrated, the record content 706 may include one or more of a provider identifier 708 (e.g., representing an entity that performed one or more services represented by the record), a service identifier 710 (e.g., representing what was performed), provider notes 712 (e.g., representing user-entered text and/or other date regarding the services performed), diagnosis information (e.g., representing whether one or more diagnoses were identified and/or entered when providing services), and/or a record identifier 716 (e.g., uniquely identifying the data record 700). It should be appreciated that, in some embodiments, the record content 706 includes any combination of the illustrated data fields, and/or one or more alternative and/or additional data fields. For example, in some embodiments, the data fields of record content 706 is dependent on the provider with which the record is associated. Additionally or alternatively, in some embodiments, the record content 706 includes procedure identification data, prescribed medication data associated with the record, and/or the like.

Example Operations Performed by Embodiments of the Disclosure

Having described an example apparatus, example systems, computing environments, and data flows, example flowcharts including various operations performed by apparatuses, devices, and/or sub-systems of the above described systems will now be discussed. It should be appreciated that each of the flowcharts depicts an example computer-implemented process that may be performed by one, or more, of the above described apparatuses, systems, or devices. In regard to the below flowcharts, one or more of the depicted blocks may be optional in some, or all, embodiments. Optional blocks may be described and/or depicted with broken (dashed) lines.

It should be appreciated that the particular operations depicted and described below with respect to FIGS. 8-12 illustrate specific operations or steps that may be performed in a particular process. Further, the process may be implemented by computing hardware, software, firmware, or a combination thereof, of a system, apparatus, device, or the like, as an implementation of a computer-implemented method. In other embodiments, the various blocks may represent blocks capable of being performed by an apparatus, device, or system. Fore example, computer-coded instructions may be specially programmed for performing the various operations depicted and stored for execution by the apparatus, for example in one or more memory devices, for execution by one or more processors. In other embodiments, computer program code capable of executing the operations depicted by the various blocks may be stored to one or more non-transitory memory devices associated with a computer program product or other computer readable storage medium.

In some embodiments, it should be appreciated that the operations described herein are performed by a label prediction system, for example embodied by an apparatus 200. In some such embodiments, a label prediction system functions automatically. In other embodiments, the user may interact with the label prediction system using one or more client devices, for example over a computer network. In this regard, the apparatus 200 embodying the label prediction system may automatically perform such operations, or being one or more operations described in response to user interaction from the client device(s). It should be appreciated that all such embodiments are to be within the scope of the disclosure herein.

Figure 8:
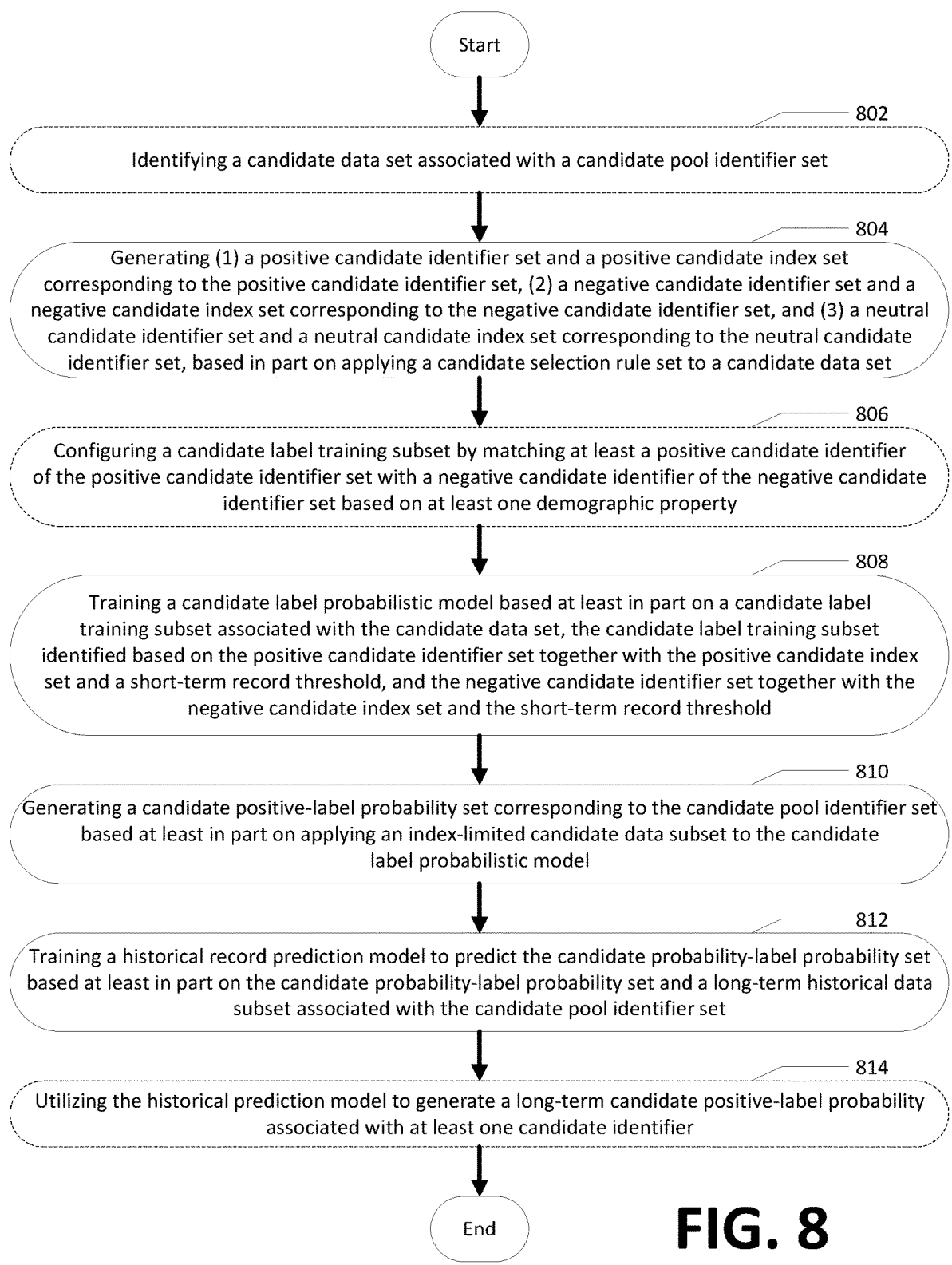

FIG. 8 illustrates an example process for label predicting using a dual-model system in accordance with example embodiments of the present disclosure. The example process illustrated may be performed by the label prediction system, for example a label prediction system 102 embodied by the apparatus 200. In some embodiments, the apparatus 200 includes or is otherwise in communication with one or more other apparatuses, systems, devices, and/or the like, to facilitate the operations described herein.

At optional block 802, the apparatus 200 includes means, such as the label prediction module 210, input/output module 206, communications module 208, processor 202, and/or the like, or a combination thereof, configured for identifying a candidate data set associated with a candidate pool identifier set. In some embodiments, the apparatus 200 is configured to identify the candidate data set by retrieving some or all of the candidate data set from a local datastore. Additionally or alternatively, in some embodiments, the apparatus 200 is configured to identify the candidate data set by retrieving some or all of the candidate data set from an external datastore. In some embodiments, the candidate data set is identified as a combination of locally stored and externally stored data records. For example, the apparatus 200 may query for one or more data records from an external datastore, and receive the data records in response to the data record. The candidate pool identifier set may represent all candidate identifiers with candidates to be scored, which may be received from a user, determined by the apparatus 200, or received from an external system. In some embodiments, the candidate data set includes at least one associated data record associated with each candidate identifier in the candidate pool identifier set.

At block 804, the apparatus 200 includes means, such as the label prediction module 210, input/output module 206, communications module 208, processor 202, and/or the like, or a combination thereof, configured for generating, based in part on applying a candidate selection rule set to a candidate data set, (1) a positive candidate identifier set and a positive candidate index set corresponding to the positive candidate identifier set, (2) a negative candidate identifier set and a negative candidate index set corresponding to the negative candidate identifier set, and (3) a neutral candidate identifier set and a neutral candidate index set corresponding to the neutral candidate identifier set. In this regard, the apparatus 200 may be configured to identify a predetermined candidate selection rule set, retrieve a candidate selection rule set, or receive a candidate selection rule set from an external system. In some embodiments, the candidate selection rule set is identified based on one or more parameter values, for example in the context of medical data analysis, a disease that generated diagnosis labels are to be associated.

At optional block 806, the apparatus 200 includes means, such as the label prediction module 210, communications module 208, processor 202, and/or the like, or a combination thereof, configured for configuring a candidate label training subset by matching at least a positive candidate identifier of the positive candidate identifier set with a negative candidate identifier of the negative candidate identifier set based on at least one demographic property. In this regard, candidate identifiers may be matched across various strata. For example, the demographic properties may include one or more of age, sex, height, weight, and/or any number of other physical or health-related factors. It should be appreciated that some or all of the candidate identifiers may be matched, as described above, to reduce reliance on the demographic property as a high level property. In some embodiments, a limited subset of the positive candidate identifier set and the negative candidate identifier set may be used for training, while one or more other subsets of the positive candidate identifier set and the negative candidate identifier set are used for validation and/or testing of the trained model.

At block 808, the apparatus 200 includes means, such as the label prediction module 210, communications module 208, processor 202, and/or the like, or a combination thereof, configured for training a candidate label probabilistic model based at least in part on a candidate label training subset associated with the candidate data set, the candidate label training subset identified based on the positive candidate identifier set together with the positive candidate index set and a short term record threshold, and the negative candidate identifier set together with the negative candidate index set and the short-term record threshold. In this regard, the candidate label training subset may include any number of candidate fact vectors generated based on a subset of the candidate data set associated with each candidate identifier and within a target data record timestamp interval. For example, a data subset may be identified for each of the positive candidate identifiers and utilized to generate a corresponding positive candidate fact vector that is then included in the candidate label training subset. The positive candidate fact vector may be Additionally or alternatively, a data subset may be identified for each of the negative candidate identifiers and utilized to generate a corresponding negative candidate fact vector that is then included in the candidate label training subset. It should be appreciated that, in some embodiments, the candidate label training subset is generated as described below with respect to FIG. 10. Additionally or alternatively, the data subsets for each of the positive candidates identifier set and the negative candidate identifier set may be index-limited based on the corresponding index dates for each candidate identifier. In this regard, the data subsets may be identified as described below with respect to FIG. 11.

In some embodiments, the apparatus 200 is configured with a predetermined short-term record threshold. In other embodiments, the apparatus 200 receives the short-term record threshold from a user or external system and/or retrieves the short-term record threshold from a datastore or configuration location in memory. For example, in some embodiments, the short-term record threshold is defined by the candidate selection rule set.

At block 810, the apparatus 200 includes means, such as the label prediction module 210, communications module 208, processor 202, and/or the like, or a combination thereof, configured for generating a candidate positive-label probability set corresponding to the candidate pool identifier set based at least in part on applying an index-limited candidate data subset to the candidate label probabilistic model. In this regard, the candidate positive-label probability set may include a candidate positive-label probability for each candidate identifier, regardless of the preliminary set that the candidate identifier was included (e.g., the positive candidate identifier set, the neutral candidate identifier set, and/or the negative candidate identifier set). In this regard, the candidate label probabilistic model is configured to generate scores for all candidate identifiers, improving the total scored candidate identifiers as compared to conventional methodologies. The candidate positive-label probability for a given candidate identifier represents the probability that the data records that fall within a desired timestamp interval (e.g., between an index date for a particular candidate identifier and a critical date before the index date based on a short-term record threshold) corresponding to the candidate identifier indicate the candidate identifier should be associated with a particular label (e.g., a first label indicating diagnosis of a disease, and/or associated with a "case" label associated with a particular cohort for purposes of a RCT). In some such embodiments, the apparatus 200 is configured to generate a candidate fact vector for each candidate identifier to be applied to the candidate label probabilistic model. It should be appreciated that, in some embodiments, the candidate positive-label probability set comprises candidate positive-label probabilities for a test set of the candidate pool identifier set.

At block 812, the apparatus 200 includes means, such as the label prediction module 210, communications module 208, processor 202, and/or the like, or a combination thereof, configured for training a historical record prediction model to predict the candidate positive-label probability set based at least in part on the candidate positive-label probability set and a long-term historical data subset associated with the candidate pool identifier set. In some embodiments, for example, the apparatus 200 is configured to identify a long-term record threshold, for example a predetermined long-term record threshold, a received long-term record threshold, or a retrieved long-term record threshold. In some embodiments, the apparatus 200 similarly identifies the long-term record threshold based on the candidate selection rule set. The apparatus 200 may utilize the long-term record threshold to generate a long-term critical date for each candidate identifier, for example where the long-term critical date is offset from the index date associated with the candidate identifier by the long-term record threshold. In some such embodiments, the apparatus 200 is configured to identify the candidate data records of the candidate data set that fall on-or-before the index date for a candidate identifier, and on-or-after the long-term critical date, for processing. These candidate data records may be analyzed to generate one or more long-term candidate fact vectors for use in training the historical record prediction model. For example, the candidate positive-label probability set for each candidate identifier may be provided together with a long-term candidate fact vector as input to train the historical record prediction model. It should be appreciated that, as described above, the historical record prediction model may be configured in any of a myriad of ways and utilizing any of a myriad of machine learning implementations.

At optional block 814, the apparatus 200 includes means, such as the label prediction module 210, communications module 208, processor 202, and/or the like, or a combination thereof, configured for utilizing the historical prediction model to generate a long-term candidate positive-label probability associated with at least one candidate identifier. In some embodiments, the apparatus 200 is configured to utilize the historical prediction model to generate a long-term candidate positive-label probability set for all candidate identifiers in the candidate pool identifier set. Alternatively or additionally, in some embodiments, the apparatus 200 is configured to utilize the historical prediction model to generate a long-term candidate positive-label probability set for candidate identifiers in a test set. Alternatively or additionally, in some embodiments, the apparatus 200 is configured to generate a long-term candidate positive-label probability for a new candidate identifier associated with one or more corresponding candidate data records. For example, the new candidate identifier and/or corresponding candidate data records may be received from a client device in response to input by the user, retrieved from an external system, and/or the like. It should be appreciated that the apparatus 200 may be utilized for generating candidate positive-label probabilities for any number of candidate identifiers.

Figure 9:
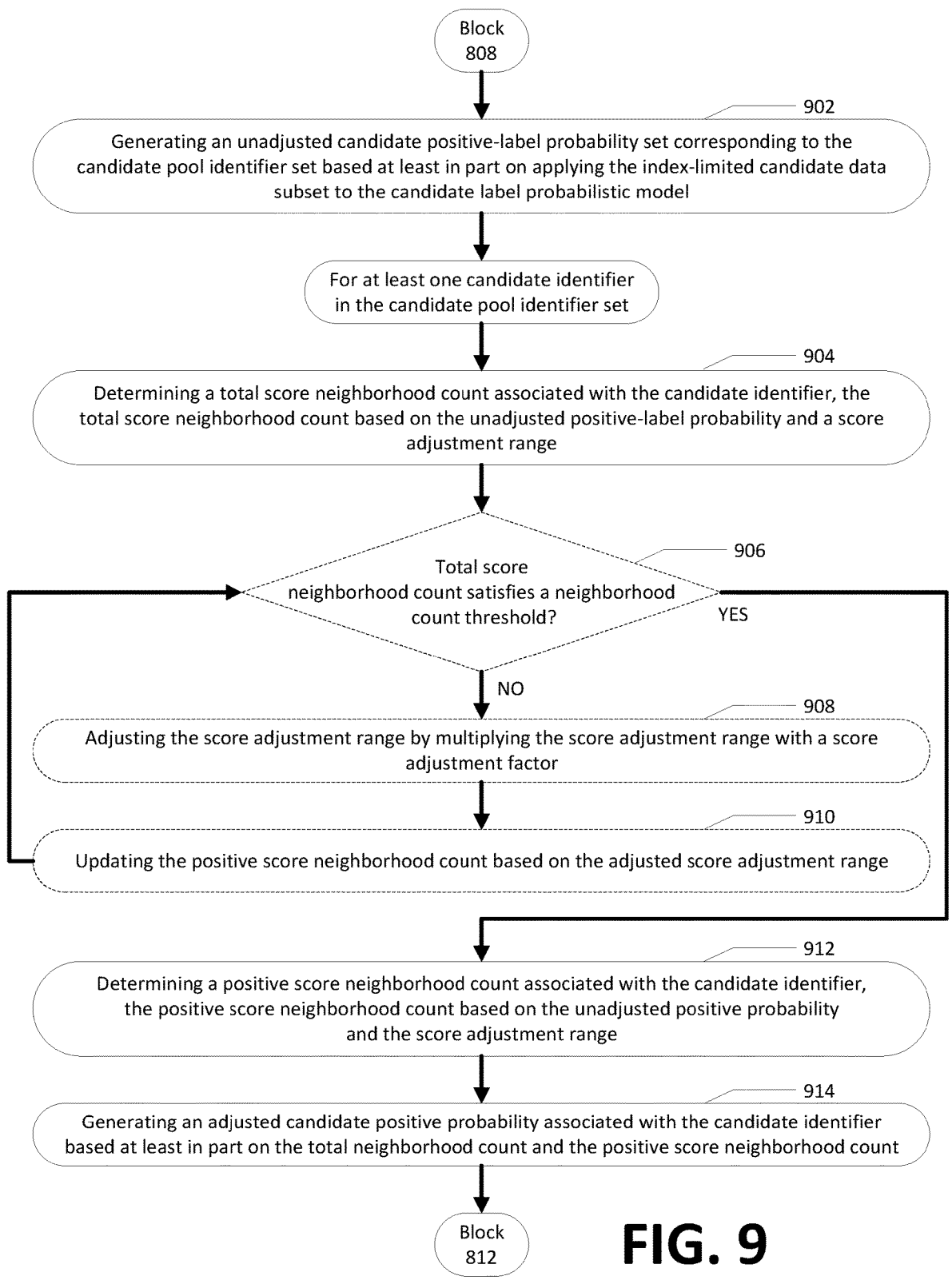

FIG. 9 illustrates additional example process for label predicting using a dual-model system, specifically for generating a well-calibrated adjusted candidate positive-label probability in accordance with example embodiments of the present disclosure. The example process illustrated may be performed by the label prediction system, for example a label prediction system 102 embodied by the apparatus 200.

In some embodiments, the apparatus 200 includes or is otherwise in communication with one or more other apparatuses, systems, devices, and/or the like, to facilitate the operations described herein.

As illustrated, the process begins at block 902, which may occur after one or more of the blocks as illustrated in FIG. 8, for example after block 808. At block 902, the apparatus 200 includes means, such as the label prediction module 210, processor 202, and/or the like, or a combination thereof, configured for generating an unadjusted candidate positive-label probability set corresponding to the candidate pool identifier set based at least in part on applying the index-limited candidate data subset to the candidate label probabilistic model. In this regard, the unadjusted candidate positive-label probability set may be generated as described above with respect to block 810. In such embodiments, the apparatus 200 may be configured to automatically proceed with post-processing of the generated unadjusted candidate positive-label probability set. For example, in some such embodiments, the apparatus 200 may be configured to initiate one or more post-processing operations, such as those described with respect to blocks 904-914, based on the implementation of the candidate label probabilistic model. For example, the operations 904-914 may be performed for adjusting unadjusted candidate positive-label probabilities generated using a deep learning model.

The operations 904-914 may be repeated for any number of candidate identifiers. For example, the operations may be performed to adjust each unadjusted candidate positive-label probability generated for each corresponding candidate identifier. In this regard, the apparatus 200 may be configured to adjust the unadjusted positive candidate probability set to generate a well-calibrated adjusted positive candidate probability set.

At block 904, the apparatus 200 includes means, such as the label prediction module 210, communications module 208, processor 202, and/or the like, or a combination thereof, configured for determining a total score neighborhood count associated with the candidate identifier, the total score neighborhood count based on the unadjusted positive-label probability for the candidate identifier and a score adjustment range. In some embodiments, the apparatus 200 is configured with a predetermined initial score adjustment range. In other embodiments, the apparatus 200 receives the score adjustment range from an external system and/or client device. In some embodiments, the score adjustment range defines a probability range (e.g., located around the unadjusted positive-label probability) for identifying other unadjusted positive-label probabilities associated with other candidate identifiers that are within the probability range. The unadjusted candidate probabilities within the probability range represent the neighborhood of the unadjusted candidate probability utilized for forming the range. In this regard, the total score neighborhood count may represent the total number of unadjusted candidate probabilities within the probability range.

At optional block 906, the apparatus 200 includes means, such as the label prediction module 210, input/output module 206, communications module 208, processor 202, and/or the like, or a combination thereof, configured for determining whether the total neighborhood count satisfies a neighborhood count threshold. In some embodiments, the apparatus 200 is configured to determine whether the total score neighborhood count satisfies the neighborhood count threshold by comparing the total score neighborhood count to the neighborhood count threshold, for example to determine if the total score neighborhood count exceeds the threshold. In this regard, the neighborhood count threshold may represent a required number of candidates to be within the probability range to maintain monotonicity. In some embodiments, the apparatus 200 is configured to identify the neighborhood count threshold, either a predetermined neighborhood count threshold or a determined neighborhood count threshold based on the candidate selection rule set. In other embodiments, the apparatus 200 is configured to receive the neighborhood count threshold or retrieve the neighborhood count threshold.

In some embodiments, in a circumstance where the apparatus 200 determines the total score neighborhood count does not satisfy the neighborhood count threshold, flow continues to block 908. At optional block 902, the apparatus 200 includes means, such as the label prediction module 210, processor 202, and/or the like, or a combination thereof, configured for adjusting the score adjustment range by multiplying the score adjustment range with a score adjustment factor. In some embodiments, the apparatus 200 identifies a predetermined score adjustment factor, receives the score adjustment factor from a client device, or retrieves the score adjustment factor from an external system. In such embodiments, the score adjustment factor may be configured to increase the size of the probability range, thus increasing the total score neighborhood count for a given candidate positive-label probability associated with a given candidate identifier. In an example embodiment, the score adjustment factor is 2, such that the score adjustment range is doubled for each adjustment. It should be appreciated that in other embodiments, the score adjustment range is adjusted through another mathematical application (e.g., division by 0.5 instead of multiplication by 2, addition of the same number instead of multiplication by 2, or the like).

At optional block 910, the apparatus 200 includes means, such as the label prediction module 210, input/output module 206, communications module 208, processor 202, and/or the like, or a combination thereof, configured for updating the positive score neighborhood count based on the adjusted score adjustment range. In this regard, the adjusted score adjustment range may be used to identify an updated probability range around the unadjusted candidate positive-label probability for the candidate identifier. The apparatus 200 may then similarly generate the updated total score neighborhood count for the updated probability range, for example as described above with respect to block 904. The updated positive score neighborhood count may then be compared again with the neighborhood count threshold, for example returning flow to block 906. If the updated total score neighborhood count still does not satisfy the neighborhood count threshold, the score adjustment factor is further adjusted for another iteration, and subsequently the positive score neighborhood count updated. The apparatus 200 may continue this routine until the total score neighborhood count is updated to a value that satisfies the neighborhood count threshold.

In a circumstance where the total score neighborhood count satisfies the neighborhood count threshold, at first iteration or after one or more updates, flow continues to block 912. At block 912, the apparatus 200 includes means, such as the label prediction module 210, processor 202, and/or the like, or a combination thereof, configured for determining a positive score neighborhood count associated with the candidate identifier, the positive score neighborhood count based on the unadjusted positive-label probability, the score adjustment range, and a positive-label probability threshold. In this regard, the positive score neighborhood count represents all other unadjusted candidate positive-label probabilities within the probability range defined by the unadjusted positive-label probability and the score adjustment range, where the unadjusted candidate positive-label probability is associated with a positive candidate identifier (e.g., assigned a preliminary label of "confirmed case"). In an example context of RCT candidates, the positive score neighborhood count reflects the number of "confirmed cases" within a particular probability range from a selected candidate positive-label probability.

At block 914, the apparatus 200 includes means, such as the label prediction module 210, 202, and/or the like, or a combination thereof, configured for generating an adjusted candidate positive-label probability associated with the candidate identifier based at least in part on the total neighborhood count and the positive score neighborhood count. In this regard, the adjusted candidate positive-label probability represents a well-calibrated probability associated with the candidate identifier. In some embodiments, the apparatus 200 generates the adjusted candidate positive-label probability using the ratio of the positive score neighborhood count to the total neighborhood count. The apparatus 200 may subsequently add the generated adjusted candidate positive-label probability, linked to the candidate identifier, to an adjusted candidate probability set.

In some embodiments, after completion of block 914, the flow ends. In other embodiments, after completion of block 914 the flow returns a subsequent block in another flow, for example to block 812 as illustrated. In yet other embodiments, after completion of block 914, the flow continues to the beginning of any of the flows described herein with respect to one of the above or below-described flows.

Figure 10:
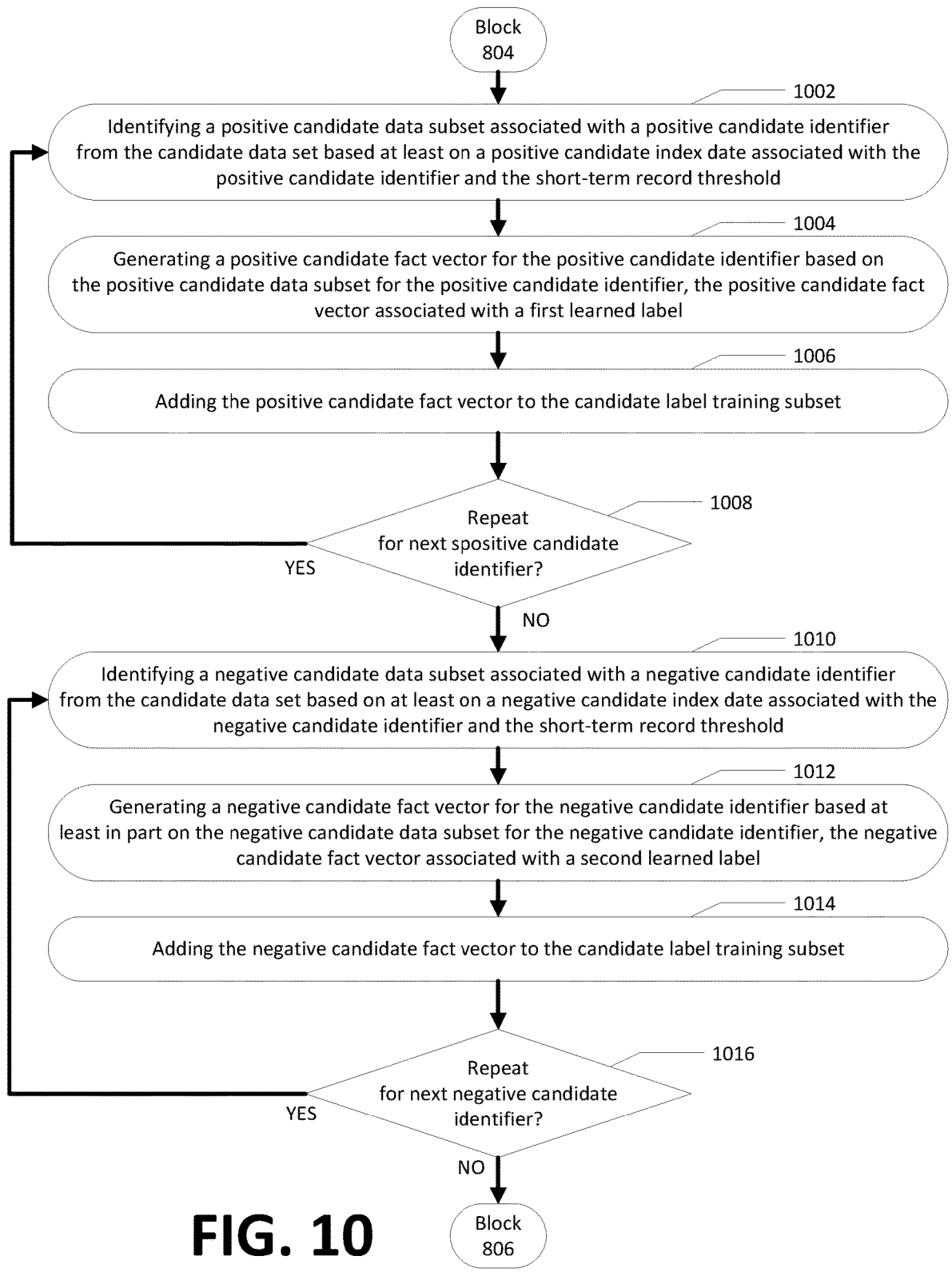

FIG. 10 illustrates additional example process for label predicting using a dual-model system, specifically for generating a candidate label training subset for training a candidate label probabilistic model in accordance with example embodiments of the present disclosure. The example process illustrated may be performed by the label prediction system, for example a label prediction system 102 embodied by the apparatus 200. In some embodiments, the apparatus 200 includes or is otherwise in communication with one or more other apparatuses, systems, devices, and/or the like, to facilitate the operations described herein.

In some embodiments, as illustrated, the flow begins at block 1002. FIG. 10 illustrates additional example process for label predicting using a dual-model system, specifically for generating a well-calibrated adjusted candidate positive-label probability in accordance with example embodiments of the present disclosure. The example process illustrated may be performed by the label prediction system, for example a label prediction system 102 embodied by the apparatus 200. In some embodiments, the apparatus 200 includes or is otherwise in communication with one or more other apparatuses, systems, devices, and/or the like, to facilitate the operations described herein.

As illustrated, the process begins at block 1002, which may occur after one or more of the blocks as illustrated in FIG. 8, for example after block 804. At block 1002, the apparatus 200 includes means, such as the label prediction module 210, input/output module 206, communications module 208, processor 202, and/or the like, or a combination thereof, configured for identifying a positive candidate subset associated with a positive candidate identifier from the candidate data set based at least on a positive candidate index date associated with the positive candidate identifier and the short-term record threshold. In some embodiments, the apparatus 200 is configured to utilize the positive candidate index date and the short-term record threshold to generate, or otherwise identify, a critical date. For example, the critical date may represent a date the short-term record threshold before the positive candidate index date. The critical date and index date may represent a particular timestamp interval within which data records associated with the positive candidate data subset may be identified and used for processing. In this regard, it should be appreciated that the timestamp interval represented by the critical date and positive candidate index date may be different for one or more candidate identifiers, as each positive candidate identifier may be associated with a different positive candidate index date.

At block 1004, the apparatus 200 includes means, such as the label prediction module 210, processor 202, and/or the like, or a combination thereof, configured for generating a positive candidate fact vector for the positive candidate identifier based on the positive candidate data subset for the positive candidate identifier, the positive candidate fact vector associated with a first learned label. The positive candidate fact vector may include any of a number of determinable healthcare related facts. In this regard, the apparatus 200 may be configured to process the positive candidate data subset for the positive candidate identifier to determine whether one or more facts is present based on the data values of each data record. The positive candidate fact vector may include engineered facts and/or be based on any number of data analysis algorithms accessible to the apparatus 200. In this regard, the positive candidate fact vector indicates facts that may be used by the apparatus 200 in training a positive candidate label probabilistic model to identify candidates that should be associated with a first learned label. In an example context of medical data analysis for RCT candidates, the first learned label may be a "case" label associated with all positive candidate identifiers.

At block 1006, the apparatus 200 includes means, such as the label prediction module 210, input/output module 206, communications module 208, processor 202, and/or the like, or a combination thereof, configured for adding the positive candidate fact vector to the candidate label training subset. In this regard, the apparatus 200 may be configured to maintain the candidate label training subset including generated the positive candidate fact vector associated with their corresponding positive candidate identifier. In some embodiments, the apparatus 200 is configured to automatically associate all positive candidate fact vectors in the candidate label training subset with the first learned label, for example by storing the positive candidate fact vectors in a separate subset from one or more generated negative candidate fact vectors as described below.

At block 1008, the apparatus 200 includes means, such as the label prediction module 210, input/output module 206, communications module 208, processor 202, and/or the like, or a combination thereof, configured for determining whether to repeat the operations for a next positive candidate identifier. In some embodiments, the apparatus 200 is configured to repeat operations 1002-1006 for all candidate identifiers in a positive candidate identifier set. In other embodiments, the apparatus 200 is configured to repeat operations 1002-1006 for a training subset of the positive candidate identifier set. If the apparatus 200 determines the operations should be repeated for the next positive candidate identifier, flow returns to block 1002 for processing based on the next positive candidate identifier. Otherwise, flow continues to block 1010.

At block 1010, the apparatus 200 includes means, such as the label prediction module 210, input/output module 206, communications module 208, processor 202, and/or the like, or a combination thereof, configured for identifying a negative candidate subset associated with a negative candidate identifier from the candidate data set based at least on a negative candidate index date associated with the negative candidate identifier and the short-term record threshold. In this regard, the negative candidate data subset is similarly constructed as described above with respect to the positive candidate data subset in block 1002. However, for the negative candidate identifier, the negative index date is not a diagnosis date, but rather a randomly selected and/or predetermined index date. Nonetheless, in this regard, the critical date and index date for the negative candidate identifier may represent a particular timestamp interval within which data records associated with the negative candidate data subset may be identified and used for processing. It should again be appreciated that the timestamp interval represented by the critical date and negative candidate index date may be different for one or more negative candidate identifiers, as each negative candidate identifier may be associated with a different negative candidate index date.

At block 1012, the apparatus 200 includes means, such as the label prediction module 210, processor 202, and/or the like, or a combination thereof, configured for generating a negative candidate fact vector for the negative candidate identifier based on the negative candidate data subset for the negative candidate identifier, the negative candidate fact vector associated with a second learned label. In some embodiments, the negative candidate fact vector includes values for the same determinable facts for the positive candidate fact vector described above with respect to block 1004. In this regard, the negative candidate fact vector indicates facts that may be used by the apparatus 200 in training a positive candidate label probabilistic model to identify candidates that should be associated with a second learned label. In an example context of medical data analysis for RCT candidates, the second learned label may be a "control" label associated with all negative candidate identifiers.

At block 1014, the apparatus 200 includes means, such as the label prediction module 210, input/output module 206, communications module 208, processor 202, and/or the like, or a combination thereof, configured for adding the negative candidate fact vector to the candidate label training subset. In this regard, the apparatus 200 may be configured to maintain the candidate label training subset including generated the negative candidate fact vector associated with its corresponding negative candidate identifier. In some embodiments, the apparatus 200 is configured to automatically associate all negative candidate fact vectors in the candidate label training subset with the second learned label, for example by storing the negative candidate fact vectors in a separate subset from one or more generated positive candidate fact vectors as described above.

At block 1016, the apparatus 200 includes means, such as the label prediction module 210, input/output module 206, communications module 208, processor 202, and/or the like, or a combination thereof, configured for determining whether to repeat the operations 1010-1014 for a next negative candidate identifier. In some embodiments, the apparatus 200 is configured to repeat operations 1010-1014 for all candidate identifiers in a negative candidate identifier set. In other embodiments, the apparatus 200 is configured to repeat operations 1010-1014 for a training subset of the negative candidate identifier set. In an example circumstance where the apparatus 200 determines the operations should be repeated for the next positive candidate identifier (e.g., a negative candidate identifier set includes an unprocessed candidate identifier), flow returns to block 1010 for processing based on the next negative candidate identifier. Otherwise, in a circumstance where the apparatus 200 determines the operations should not be repeated, the flow continues.

In some embodiments, after completion of block 1016, the flow ends. In other embodiments, after completion of block 1016 the flow returns a subsequent block in another flow, for example to block 806 as illustrated. In yet other embodiments, after completion of block 1016, the flow continues to the beginning of any of the flows described herein with respect to one of the above or below-described flows.

Figure 11:
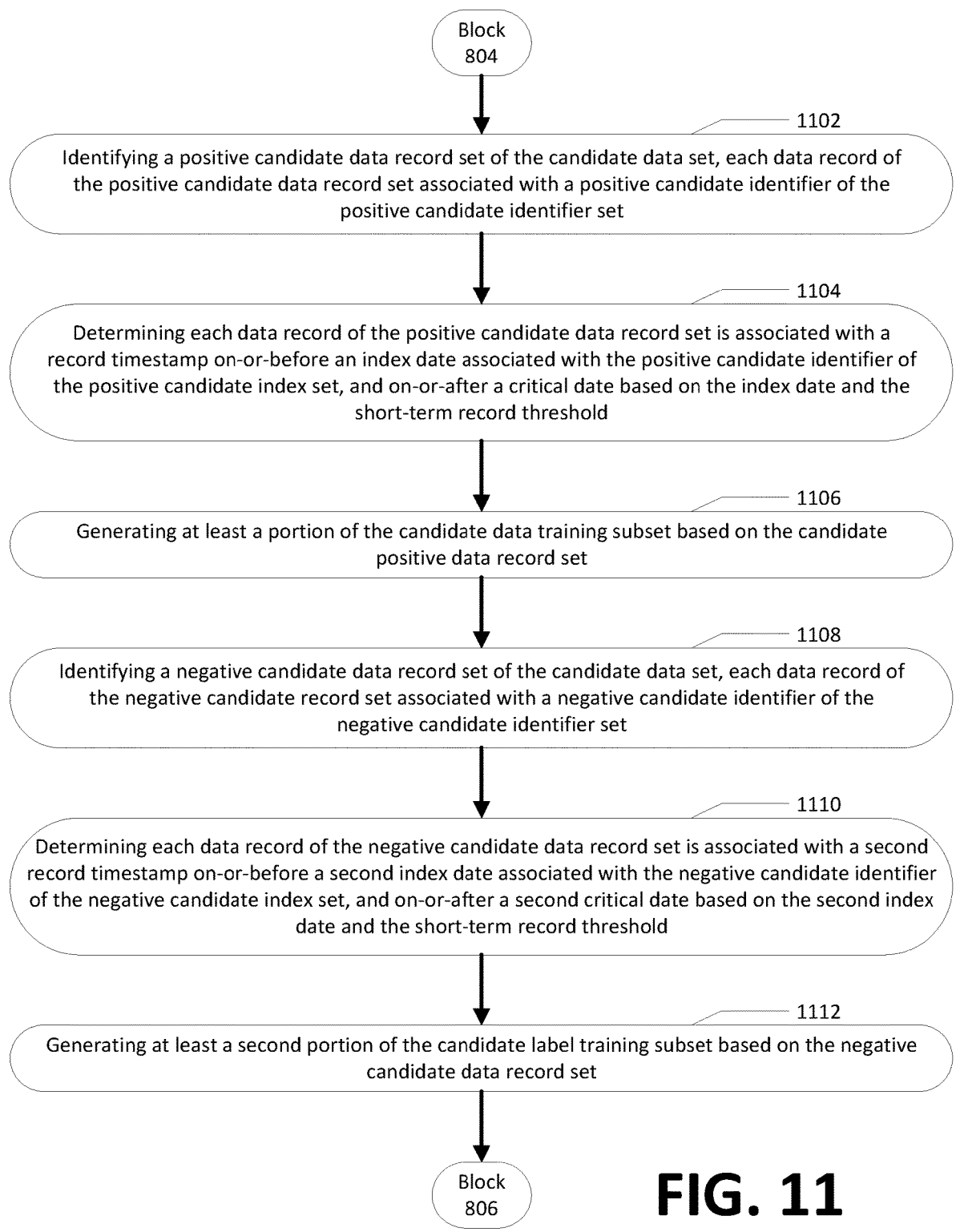

FIG. 11 illustrates additional example process for label predicting using a dual-model system, specifically for generating a candidate label training subset based on one or more index-limited data subsets in accordance with example embodiments of the present disclosure. The example process illustrated may be performed by the label prediction system, for example a label prediction system 102 embodied by the apparatus 200. In some embodiments, the apparatus 200 includes or is otherwise in communication with one or more other apparatuses, systems, devices, and/or the like, to facilitate the operations described herein.

As illustrated, the process begins at block 1102, which may occur after one or more of the blocks as illustrated in FIG. 8, for example after block 804. At block 1102, the apparatus 200 includes means, such as the label prediction module 210, input/output module 206, communications module 208, processor 202, and/or the like, or a combination thereof, configured for identifying a positive candidate data record set of the candidate data set, each data record of the positive candidate data record set associated with a positive candidate identifier of the positive candidate identifier set. In some embodiments, for example, the apparatus 200 is configured to query the candidate data set based on the positive candidate identifier. In response to the query, the apparatus 200 may identify and/or receive response data including the positive candidate data record set for the positive candidate identifier. In some embodiments, the apparatus 200 is configured to query one or more datastores, for example one or more local and/or external datastore, to identify the positive candidate data record set.

At block 1104, the apparatus 200 includes means, such as the label prediction module 210, processor 202, and/or the like, or a combination thereof, configured for determining each data record of the positive candidate data record set is associated with a record timestamp on-or-before an index date, associated with the positive candidate identifier, of the positive candidate index set, and on-or-after a critical date based on the index date and the short-term record threshold. For example, the apparatus 200 may identify an index date associated with the positive candidate identifier by retrieving a corresponding index date from the positive candidate index set using the positive candidate identifier. Additionally, as described above, the apparatus 200 may generate, identify, or otherwise determine the critical date by determining a timestamp that is the short-term record threshold before the index date. In this regard, the apparatus 200 may be configured to identify the critical date using timestamp manipulation operations (e.g., where index date−short-term record threshold=critical date). In some such embodiments, the apparatus 200 is configured to query the positive candidate data record set for data records associated with a timestamp interval represented by the index date and critical date. In some embodiments, each data record not within the desired timestamp interval is not added to the positive candidate data record set and/or otherwise removed from the positive candidate data record set.

At block 1106, the apparatus 200 includes means, such as the label prediction module 210, processor 202, and/or the like, or a combination thereof, configured for generating at least a portion of the candidate data training subset based on the positive candidate data record set. In some embodiments, for example, the apparatus 200 generates a first portion of the candidate data training subset that includes all positive candidate data records within the desired timestamp interval. In other embodiments, the apparatus 200 generates the first portion of the candidate data training subset that includes a portion of the positive candidate data records within the desired timestamp interval. For example, the apparatus 200 may determine a training positive candidate identifier set, and include only data records associated with candidate identifiers in the training positive candidate identifier set within the desired timestamp interval.

It should be appreciated that the operations 1102-1106 may similarly be repeated for any number of positive candidate identifiers. For example, in at least one embodiment, the apparatus 200 is configured to repeat the operations described for at least one other positive candidate identifier in a training positive candidate identifier set.

At block 1108, the apparatus 200 includes means, such as the label prediction module 210, input/output module 206, communications module 208, processor 202, and/or the like, or a combination thereof, configured for identifying a negative candidate data record set of the candidate data set, each data record of the negative candidate data record set associated with a negative candidate identifier of the negative candidate identifier set. In some embodiments, for example, the apparatus 200 is configured to query the candidate data set based on the negative candidate identifier. In response to the query, the apparatus 200 may identify and/or receive response data including the negative candidate data record set for the negative candidate identifier. In some embodiments, the apparatus 200 is configured to query one or more datastores, for example one or more local and/or external datastore, to identify the negative candidate data record set.

At block 1110, the apparatus 200 includes means, such as the label prediction module 210, processor 202, and/or the like, or a combination thereof, configured for determining each data record of the negative candidate data record set is associated with a second record timestamp on-or-before a second index date, associated with the negative candidate identifier, of the negative candidate index set, and on-or-after a second critical date based on the second index date and the short-term record threshold. For example, the apparatus 200 may identify a second index date associated with the negative candidate identifier by retrieving a corresponding second index date from the negative candidate index set using the negative candidate identifier. Additionally, as described above, the apparatus 200 may similarly generate, identify, or otherwise determine the second critical date by determining a timestamp that is the short-term record threshold before the second index date. In some such embodiments, the apparatus 200 is configured to query the negative candidate data record set for data records associated with a timestamp interval represented by the second index date and second critical date. In some embodiments, each data record not within the desired timestamp interval is not added to the negative candidate data record set and/or otherwise removed from the negative candidate data record set, for not falling within the desired timestamp interval.

At block 1112, the apparatus 200 includes means, such as the label prediction module 210, processor 202, and/or the like, or a combination thereof, configured for generating at least a second portion of the candidate data training subset based on the negative candidate data record set. In some embodiments, for example, the apparatus 200 generates the second portion of the candidate data training subset that includes all negative candidate data records within the timestamp interval. In other embodiments, the apparatus 200 generates the second portion of the candidate data training subset that includes a portion of the negative candidate data records within the timestamp interval. For example, the apparatus 200 may determine a training negative candidate identifier set, and include only data records associated with candidate identifiers in the training negative candidate identifier set that are within the timestamp interval.

It should be appreciated that the operations 1108-1112 may similarly be repeated for any number of negative candidate identifiers. For example, in at least one embodiment, the apparatus 200 is configured to repeat the operations described for at least one other negative candidate identifier in a training negative candidate identifier set.

In some embodiments, after completion of block 1112, the flow ends. In other embodiments, after completion of block 1112 the flow returns a subsequent block in another flow, for example to block 806 as illustrated. In yet other embodiments, after completion of block 1112, the flow continues to the beginning of any of the flows described herein with respect to one of the above or below-described flows.

Figure 12:
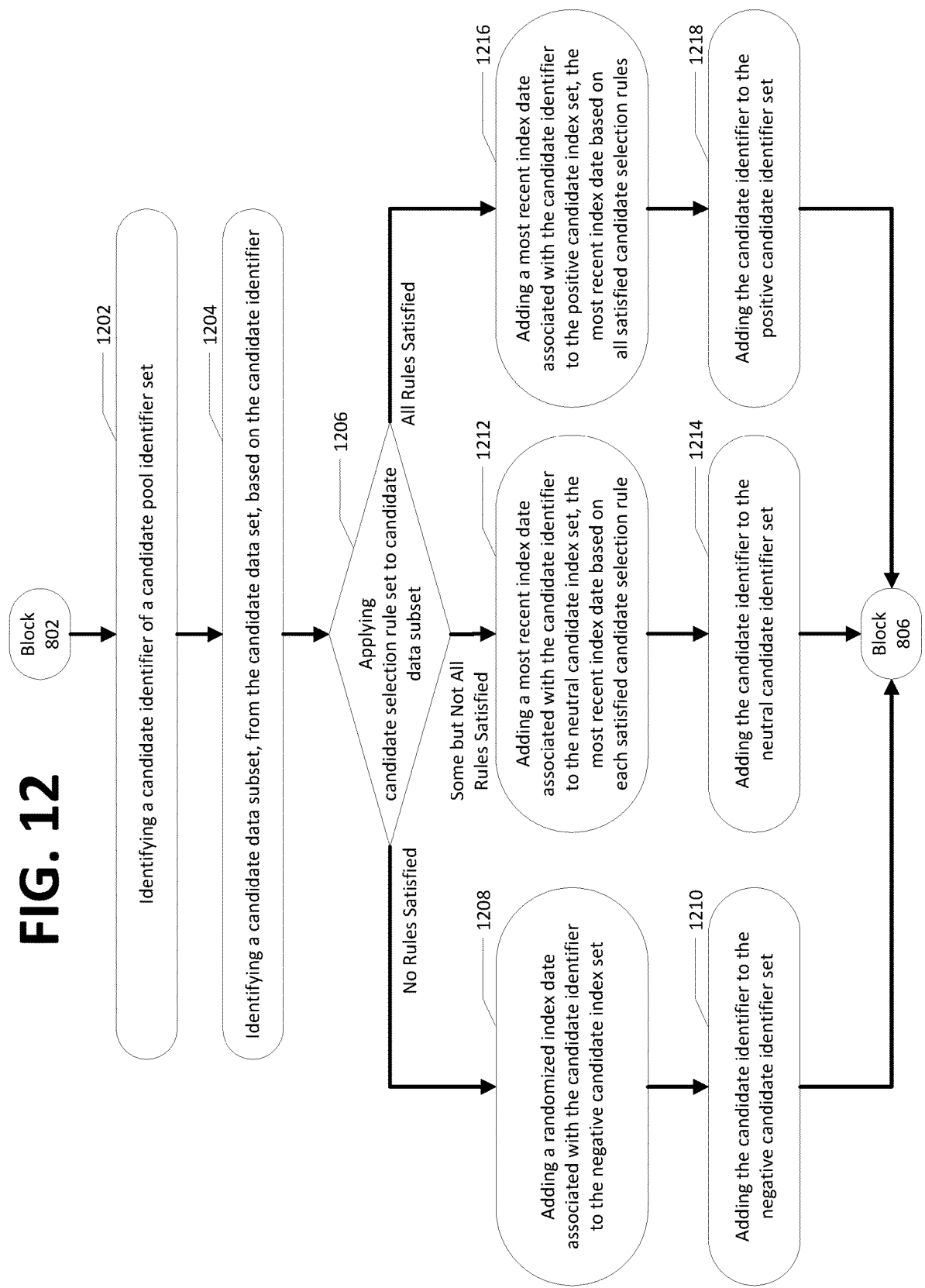

FIG. 12 illustrates additional example process for label predicting using a dual-model system, specifically for generating a positive, neutral, and negative candidate index set, and a positive, negative, and neutral identifier set, in accordance with example embodiments of the present disclosure. The example process illustrated may be performed by the label prediction system, for example a label prediction system 102 embodied by the apparatus 200. In some embodiments, the apparatus 200 includes or is otherwise in communication with one or more other apparatuses, systems, devices, and/or the like, to facilitate the operations described herein.

As illustrated, the process begins at block 1102, which may occur after one or more of the blocks as illustrated in FIG. 8, for example after block 802. At block 1202, the apparatus 200 includes means, such as the label prediction module 210, input/output module 206, communications module 208, processor 202, and/or the like, or a combination thereof, configured for identifying a candidate identifier of the candidate pool identifier set. In some embodiments, the apparatus 200 is configured with a predetermined candidate pool identifier set. In other embodiments, the apparatus 200 receives and/or retrieves the candidate pool identifier set. The apparatus 200 may subsequently perform the operations depicted with respect to FIG. 12 for each of the candidate identifiers in the candidate pool identifier set (for example, in order), or for one or more predetermined candidate identifiers within the candidate pool identifier set.

At block 1204, the apparatus 200 includes means, such as the label prediction module 210, input/output module 206, communications module 208, processor 202, and/or the like, or a combination thereof, configured for identifying a candidate data subset, from the candidate data set, based on the candidate identifier. In this regard, the candidate data subset from the candidate data set may include all data records associated with the candidate identifier. In some embodiments, the apparatus 200 queries the candidate data set for data records based on the candidate identifier (e.g., data records that include the candidate identifier as the value for a particular data field of the data record), and receives the candidate data subset as response data to the query. As described above, the apparatus 200 may query one or more local datastores and/or external datastores to identify the candidate data subset from the candidate data set.

At block 1206, the apparatus 200 includes means, such as the label prediction module 210, input/output module 206, communications module 208, processor 202, and/or the like, or a combination thereof, configured for determining whether the candidate data subset satisfies one or more rules of a candidate selection rule set by applying the candidate selection rule set to the candidate data subset. In this regard, the apparatus 200 may be configured to process the candidate data subset based on one or more electronically performed algorithms defining the candidate selection rule set. It should be appreciated that the candidate selection rule set may include any number of data record processing algorithms that may be expressed via particular computer-coded instructions, for example, for execution by the apparatus 200. In some embodiments, the apparatus 200 is preconfigured to perform particular algorithms embodying the candidate selection rule set. In other embodiments, the apparatus 200 is configured to retrieve and/or receive information from one or more associated systems and/or external systems embodying the candidate selection rule set.

In an example context, the apparatus 200 is configured to determine a certain number of rules are satisfied, and perform one or more subsequent actions based on the determination. For example, in some embodiments, the apparatus 200 is configured to perform a first set of operations in a circumstance where the apparatus 200 determines the candidate data subset satisfies no rules of the candidate selection rule set, perform a second set of operations in a circumstance where the apparatus 200 determines the candidate data subset satisfies at least one but not all rules of the candidate selection rule set, and perform a third set of operations in a circumstance where the apparatus 200 determines the candidate data subset satisfies all rules (or above a particular threshold) of the candidate selection rule set.

As illustrated, in a circumstance where the apparatus 200 determines the candidate data subset satisfies no rules of the candidate selection rule set, flow continues to block 1208. At block 1208, the apparatus 200 includes means, such as the label prediction module 210, input/output module 206, communications module 208, processor 202, and/or the like, or a combination thereof, configured for adding a randomized index date associated with the candidate identifier to the negative candidate index set. In some embodiments, the apparatus 200 generates the randomized index date by selecting a random data record of the candidate data subset, and utilizing the data record timestamp associated with the random data record as the index date. Alternatively, in some embodiments, the apparatus 200 is configured to select a pre-determined data record (e.g., the $10^{th}$ most recent data record) and utilizing the data record timestamp associated with the selected data record as the index date. The apparatus 200 may maintain the link between the candidate identifier and the randomized index date in the negative candidate index set, such that the randomized index date may be retrieved from the negative candidate index set using the candidate identifier.

At block 1210, the apparatus 200 includes means, such as the label prediction module 210, input/output module 206, communications module 208, processor 202, and/or the like, or a combination thereof, configured for adding the candidate identifier to the negative candidate identifier set. In this regard, the negative candidate identifier set may represent candidate identifiers confirmed as associated with a second learned label. For example, in the context of RCT candidates, the negative candidate identifier set may include candidate identifiers to be associated with a label of "confirmed control." In this regard, the negative candidate identifiers in the negative candidate identifier set are confirmed as not diagnosed with a corresponding disease, for example based on failing to meet any of the rules for diagnosis of that disease.

Alternatively, as illustrated, in a circumstance where the apparatus 200 determines the candidate data subset satisfies at least one but not all of the candidate selection rule set, flow continues to block 1212. At block 1212, the apparatus 200 includes means, such as the label prediction module 210, input/output module 206, communications module 208, processor 202, and/or the like, or a combination thereof, configured for adding a most recent index date associated with the candidate identifier to the neutral candidate index set, the most recent index date based on each satisfied candidate selection rule. In this regard, the apparatus 200 may determine the most recent data record timestamp for a data record utilized in satisfying one of the satisfied candidate selection rules. In such embodiments, the most recent index represents the data record timestamp for the most recent data record used in satisfying any of the candidate selection rules. For example, in some embodiments, the apparatus 200 is configured to identify the data record timestamp for each data record of the candidate data subset utilized in determining a candidate selection rule of the candidate selection rule set is satisfied, and select the most recent of the identified data record timestamps based on one or more comparisons.

At block 1214, the apparatus 200 includes means, such as the label prediction module 210, input/output module 206, communications module 208, processor 202, and/or the like, or a combination thereof, configured for adding the candidate identifier to the neutral candidate identifier set. In this regard, the neutral candidate identifier set may represent candidate identifiers unconfirmed as associated with either a first learned label or a second learned label. For example, in the context of RCT candidates, the neutral candidate identifier set may include candidate identifiers to be associated with a label of "unconfirmed." In this regard, the neutral candidate identifiers in the neutral candidate identifier set are unconfirmed as diagnosed or not diagnosed with a corresponding disease, for example based on meeting one but not all of the rules for diagnosis of that disease.

Alternatively, as illustrated, in a circumstance where the apparatus 200 determines the candidate data subset satisfies all of the candidate selection rule set, flow continues to block 1216.

At block 1216, the apparatus 200 includes means, such as the label prediction module 210, input/output module 206, communications module 208, processor 202, and/or the like, or a combination thereof, configured for adding a most recent index date associated with the candidate identifier to the positive candidate index set, the most recent index date based all satisfied candidate selection rules. In this regard, the apparatus 200 may determine the most recent data record timestamp for any data record utilized in satisfying the most-recently satisfied candidate selection rule. In this regard, the apparatus 200 is configured to perform the data record timestamp identification steps and comparison described above with respect to block 1212 for all candidate selection rules.

At block 1218, the apparatus 200 includes means, such as the label prediction module 210, input/output module 206, communications module 208, processor 202, and/or the like, or a combination thereof, configured for adding the candidate identifier to the positive candidate identifier set. In this regard, the positive candidate identifier set may represent candidate identifiers confirmed as associated a first learned label. For example, in the context of RCT candidates, the positive candidate identifier set may include candidate identifiers to be associated with a label of "confirmed case." In this regard, the positive candidate identifiers in the positive candidate identifier set are confirmed as diagnosed with a corresponding disease, for example based on meeting all rules for diagnosis of that disease.

It should be appreciated that operations 1202-1218 may be repeated for any number of candidate identifiers. For example, in some embodiments, the apparatus 200 is configured to repeat the operations described for all candidate identifiers in a candidate pool identifier set. In this regard, the apparatus 200 is configured to generate a complete negative, neutral, and positive candidate identifier sets, along with corresponding index sets, for further processing. For example, the apparatus 200 may utilize specific subsets, for example the negative candidate identifier set and the positive candidate identifier set, for purposes of training the candidate label probabilistic model as described above.

In some embodiments, after completion of block 1210, 1214, or 1218, the flow ends. In other embodiments, after completion of block 1210, 1214, or 1218, the flow returns a subsequent block in another flow, for example to block 806 as illustrated. In yet other embodiments, after completion of block 1210, 1214, or 1218, the flow continues to the beginning of any of the flows described herein with respect to one of the above or below-described flows.

CONCLUSION

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., a FPGA or an ASIC. The apparatus can also include, in addition to hardware, code that creates an execution environment for the computer program in question, e.g., code that constitutes processor firmware, a protocol stack, a repository management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method, the method comprising:

generating, based at least in part on applying a candidate selection rule set to a candidate data set, (1) a positive candidate identifier set. (2) a positive candidate index set corresponding to the positive candidate identifier set, (3) a negative candidate identifier set, (4) a negative candidate index set corresponding to the negative candidate identifier set,(5) a neutral candidate identifier set, and (6) a neutral candidate index set corresponding to the neutral candidate identifier set, wherein the candidate data set is associated with a candidate pool identifier set comprising the positive candidate identifier set, negative candidate identifier set, and neutral candidate identifier set;

training a candidate label probabilistic model based at least in part on a candidate label training subset associated with the candidate data set, wherein the candidate label training subset is identified based at least in part on (1) the positive candidate identifier set together with the positive candidate index set and a short-term record threshold, and (2) the negative candidate identifier set together with the negative candidate index set and the short-term record threshold;

generating a candidate positive-label probability set corresponding to the candidate pool identifier set based at least in part on applying an index-limited candidate data subset to the candidate label probabilistic model, wherein the index-limited candidate data subset is based at least in part on (1) the positive candidate identifier set together with the positive candidate index set and the short-term record threshold, (2) the negative candidate identifier set together with the negative candidate index set and the short-term record threshold, and (3) the neutral candidate identifier set together with the neutral candidate index set and the short-term record threshold;

training a historical record prediction model to predict the candidate positive-label probability set based at least in part on the candidate positive-label probability set and a long-term historical data subset associated with the candidate pool identifier set, wherein the long-term historical data subset is based at least in part on (1) the positive candidate identifier set together with the positive candidate index set and a long-term record threshold, (2) the negative candidate identifier set together with the negative candidate index set and the long-term record threshold, and (3) the neutral candidate identifier set together with the neutral candidate index set and the long-term record threshold; and utilizing the historical record prediction model to generate a long-term candidate positive-label probability associated with at least one candidate identifier.

2. The computer-implemented method of claim 1, the method further comprising:

for each positive candidate identifier of at least a subset of the positive candidate identifier set:
- identifying a positive candidate data subset, associated with the positive candidate identifier, from the candidate data set based at least in part on a positive candidate index date associated with the positive candidate identifier and the short-term record threshold;
- generating a positive candidate fact vector for the positive candidate identifier based at least in part on the positive candidate data subset for the positive candidate identifier, the positive candidate fact vector associated with a first learned label; and
- adding the positive candidate fact vector to the candidate label training subset; and for each negative candidate identifier of at least a subset of the negative candidate identifier set:
- identifying a negative candidate data subset, associated with the negative candidate identifier, from the candidate data set based at least in part on a negative candidate index date associated with the negative candidate identifier and the short-term record threshold;
- generating a negative candidate fact vector for the positive candidate identifier based at least in part on the negative candidate data subset for the negative candidate identifier, the negative candidate fact vector associated with a second learned label; and
- adding the negative candidate fact vector to the candidate label training subset.

3. The computer-implemented method of claim 1, wherein training the candidate label probabilistic model comprises:

identifying a positive candidate data record set of the candidate data set, wherein each data record of the positive candidate data record set is associated with a positive candidate identifier of the positive candidate identifier set;

determining that each data record of the positive candidate data record set is associated with a record timestamp on or before an index date associated with the positive candidate identifier of the positive candidate index set, and on or after a critical date based at least in part on the index date and the short-term record threshold;

generating at least a portion of the candidate label training subset based at least in part on the positive candidate data record set;

identifying a negative candidate data record set of the candidate data set, wherein each data record of negative candidate data record set is associated with a negative candidate identifier of the negative candidate identifier set;

determining that each data record of the negative candidate data record set is associated with a second record timestamp on or before a second index date associated with the negative candidate identifier of the negative candidate index set, and on or after a second critical date based at least in part on the second index date and the short-term record threshold; and generating at least a second portion of the candidate label training subset based at least in part on the negative candidate data record set.

4. The computer-implemented method of claim 1, wherein applying the index-limited candidate data subset to the candidate label probabilistic model to generate the candidate positive-label probability set corresponding to candidate pool identifier set comprises:

determining an unadjusted candidate positive-label probability set corresponding to candidate pool identifier set at least in part by applying the index-limited candidate data subset to the candidate label probabilistic model;

for at least a candidate identifier in the candidate pool identifier set, wherein the candidate identifier is associated with an unadjusted positive-label probability from the unadjusted candidate positive-label probability set,
- determining a total score neighborhood count associated with the candidate identifier, the total score neighborhood count based at least in part on the unadjusted positive-label probability and a score adjustment range;
- determining a positive score neighborhood count associated with the candidate identifier, the positive score neighborhood count based at least in part on the unadjusted positive-label probability, the score adjustment range, and a positive-label probability threshold; and
- generating an adjusted candidate positive-label probability associated with the candidate identifier based at least in part on the total score neighborhood count and the positive score neighborhood count, wherein the generated candidate positive-label probability set comprises at least one adjusted candidate positive-label probability.

5. The computer-implemented method of claim 4, the method further comprising:

applying the index-limited candidate data subset to the candidate label probabilistic model to determine an unadjusted candidate positive-label probability set corresponding to candidate pool identifier set;

for at least a candidate identifier in the candidate pool identifier set, wherein the candidate identifier is associated with an unadjusted positive-label probability from the unadjusted candidate positive-label probability set,
- determining a first total score neighborhood count associated with the candidate identifier, the first total score neighborhood count based at least in part on the unadjusted positive-label probability and a score adjustment range;
- determining that the first total score neighborhood count does not satisfy a neighborhood count threshold;
- adjusting the score adjustment range by multiplying the score adjustment range with a score adjustment factor at least one time;
- determining an updated total score neighborhood count associated with the candidate identifier, the updated total score neighborhood count based at least in part on the unadjusted positive-label probability and the score adjustment range, wherein the updated total score neighborhood count satisfies the neighborhood count threshold;

determining a positive score neighborhood count associated with the candidate identifier, the positive score neighborhood count based at least in part on the unadjusted positive-label probability, the score adjustment range, and a positive-label probability threshold; and generating an adjusted candidate positive-label probability associated with the candidate identifier based at least in part on the updated total score neighborhood count and the positive score neighborhood count, wherein the generated candidate positive-label probability set comprises at least one adjusted candidate positive-label probability.

6. An apparatus comprising at least one processor and at least one non-transitory memory, the non-transitory memory including computer-coded instructions thereon, the computer-coded instructions, in execution with the at least one processor, configure the apparatus to:

generate, based at least in part on applying a candidate selection rule set to a candidate data set, (1) a positive candidate identifier set, (2) a positive candidate index set corresponding to the positive candidate identifier set, (3) a negative candidate identifier set, (4) a negative candidate index set corresponding to the negative candidate identifier set,(5) a neutral candidate identifier set, and (6) a neutral candidate index set corresponding to the neutral candidate identifier set, wherein the candidate data set is associated with a candidate pool identifier set comprising the positive candidate identifier set, negative candidate identifier set, and neutral candidate identifier set;

train a candidate label probabilistic model based at least in part on a candidate label training subset associated with the candidate data set, wherein the candidate label training subset is identified based at least in part on (1) the positive candidate identifier set together with the positive candidate index set and a short-term record threshold, and (2) the negative candidate identifier set together with the negative candidate index set and the short-term record threshold;

generate a candidate positive-label probability set corresponding to the candidate pool identifier set based at least in part on applying an index-limited candidate data subset to the candidate label probabilistic model, wherein the index-limited candidate data subset is based at least in part on (1) the positive candidate identifier set together with the positive candidate index set and the short-term record threshold, (2) the negative candidate identifier set together with the negative candidate index set and the short-term record threshold, and (3) the neutral candidate identifier set together with the neutral candidate index set and the short-term record threshold;

train a historical record prediction model to predict the candidate positive-label probability set based at least in part on the candidate positive-label probability set and a long-term historical data subset associated with the candidate pool identifier set, wherein the long-term historical data subset is based at least in part on (1) the positive candidate identifier set together with the positive candidate index set and a long-term record threshold, (2) the negative candidate identifier set together with the negative candidate index set and the long-term record threshold, and (3) the neutral candidate identifier set together with the neutral candidate index set and the long-term record threshold; and utilize the historical record prediction model to generate a long-term candidate positive-label probability associated with at least one candidate identifier.

7. The apparatus of claim 6, the apparatus further configured to:

for each positive candidate identifier of at least a subset of the positive candidate identifier set:
identify a positive candidate data subset, associated with the positive candidate identifier, from the candidate data set based at least in part on a positive candidate index date associated with the positive candidate identifier and the short-term record threshold;
generate a positive candidate fact vector for the positive candidate identifier based at least in part on the positive candidate data subset for the positive candidate identifier, the positive candidate fact vector associated with a first learned label; and
add the positive candidate fact vector to the candidate label training subset; and for each negative candidate identifier of at least a subset of the negative candidate identifier set:
identify a negative candidate data subset, associated with the negative candidate identifier, from the candidate data set based at least in part on a negative candidate index date associated with the negative candidate identifier and the short-term record threshold;
generate a negative candidate fact vector for the positive candidate identifier based at least in part on the negative candidate data subset for the negative candidate identifier, the negative candidate fact vector associated with a second learned label; and
add the negative candidate fact vector to the candidate label training subset.

8. The apparatus of claim 6, wherein to train the candidate label probabilistic model, the apparatus is configured to:
identify a positive candidate data record set of the candidate data set, wherein each data record of the positive candidate data record set is associated with a positive candidate identifier of the positive candidate identifier set;
determine that each data record of the positive candidate data record set is associated with a record timestamp on or before an index date associated with the positive candidate identifier of the positive candidate index set, and on or after a critical date based at least in part on the index date and the short-term record threshold;
generate at least a portion of the candidate label training subset based at least in part on the positive candidate data record set;
identify a negative candidate data record set of the candidate data set, wherein each data record of negative candidate data record set is associated with a negative candidate identifier of the negative candidate identifier set;
determine that each data record of the negative candidate data record set is associated with a second record timestamp on or before a second index date associated with the negative candidate identifier of the negative candidate index set, and on or after a second critical date based at least in part on the second index date and the short-term record threshold; and
generate at least a second portion of the candidate label training subset based at least in part on the negative candidate data record set.

9. The apparatus of claim 6, wherein to train the candidate label probabilistic model, the apparatus is configured to:
configure the candidate label training subset by matching at least a positive candidate identifier of the positive candidate identifier set with a negative candidate identifier of the negative candidate identifier set based at least in part on at least one demographic property; and
train the candidate label probabilistic model based at least in part on the configured candidate label training subset.

10. The apparatus of claim 6, the apparatus further configured to:
identify the candidate data set from one or more local datastores, one or more external datastores, or a combination thereof.

11. The apparatus of claim 6, wherein the candidate data set comprises a plurality of data records, each data record associated with a candidate identifier of the candidate pool identifier set and a services timestamp.

12. The apparatus of claim 6, wherein the candidate data set comprises a structured medical data record set, an unstructured medical data, or a combination thereof.

13. The apparatus of claim 6, wherein to generate the negative candidate identifier set and the negative candidate index set, the apparatus is configured to:
identify a candidate data subset associated with a candidate identifier of the candidate pool identifier set;
upon determining, based at least in part on the candidate data subset, that the candidate data subset does not satisfy any selection rule of the candidate selection rule set:
add a randomized index date associated with the candidate identifier to the negative candidate index set, the randomized index date based at least in part on the candidate data subset; and
add the candidate identifier to the negative candidate identifier set.

14. The apparatus of claim 6, wherein to generate the neutral candidate identifier set and the neutral candidate index set, the apparatus is configured to:
identify a candidate data subset associated with a candidate identifier of the candidate pool identifier set;
upon determining, based at least in part on the candidate data subset, that the candidate data subset satisfies at least one selection rule of the candidate selection rule set but does not satisfy every selection rule of the candidate selection rule set:
add a most recent index date associated with the candidate identifier to the neutral candidate index set, the most recent index date based at least in part on the at least one satisfied candidate selection rule; and
add the candidate identifier to the neutral candidate identifier set.

15. The apparatus of claim 6, wherein to generate the positive candidate identifier set and the positive candidate index set, the apparatus is configured to:
identify a candidate data subset associated with a candidate identifier of the candidate pool identifier set;
upon determining, based at least in part on the candidate data subset, that the candidate data subset satisfies at each selection rule of the candidate selection rule set:
add a most recent index date associated with the candidate identifier to the positive candidate index set, the most recent index date based at least in part on each satisfied candidate selection rule; and
add the candidate identifier to the positive candidate identifier set.

16. The apparatus of claim 6, wherein to train the candidate label probabilistic model, the apparatus is configured to:
generate a positive candidate data set based at least in part on the candidate data set, the positive candidate identifier set, and the positive candidate index set;
generate a negative candidate data set based at least in part on the candidate data set, the negative candidate identifier set, and the negative candidate index set;
generate the candidate label training subset at least in part by combining the positive candidate data set and the negative candidate data set; and
train the candidate label probabilistic model based at least in part on the candidate label training subset.

17. The apparatus of claim 6, wherein to utilize the historical record prediction model to generate the long-term candidate positive-label probability associated with at least one candidate identifier, the apparatus is configured to:
generate a historical record predictive score set at least in part by applying the candidate data set to the historical record prediction model.

18. The apparatus of claim 6, wherein to apply the index-limited candidate data subset to the candidate label probabilistic model to generate the candidate positive-label probability set corresponding to candidate pool identifier set, the apparatus is configured to:
determine an unadjusted candidate positive-label probability set corresponding to candidate pool identifier set at least in part by applying the index-limited candidate data subset to the candidate label probabilistic model;
for at least a candidate identifier in the candidate pool identifier set, wherein the candidate identifier is associated with an unadjusted positive-label probability from the unadjusted candidate positive-label probability set,
determine a total score neighborhood count associated with the candidate identifier, the total score neighborhood count based at least in part on the unadjusted positive-label probability and a score adjustment range;
determine a positive score neighborhood count associated with the candidate identifier, the positive score neighborhood count based at least in part on the unadjusted positive-label probability, the score adjustment range, and a positive-label probability threshold; and
generate an adjusted candidate positive-label probability associated with the candidate identifier based at least in part on the total score neighborhood count and the positive score neighborhood count,
wherein the generated candidate positive-label probability set comprises at least one adjusted candidate positive-label probability.

19. The apparatus of claim 18, the apparatus further configured to:
apply the index-limited candidate data subset to the candidate label probabilistic model to determine an unadjusted candidate positive-label probability set corresponding to candidate pool identifier set;
for at least a candidate identifier in the candidate pool identifier set, wherein the candidate identifier is associated with an unadjusted positive-label probability from the unadjusted candidate positive-label probability set, determine a first total score neighborhood count associated with the candidate identifier, the first total score neighborhood count based at least in part on the unadjusted positive-label probability and a score adjustment range;

determine that the first total score neighborhood count does not satisfy a neighborhood count threshold;

adjust the score adjustment range by multiplying the score adjustment range with a score adjustment factor at least one time;

determine an updated total score neighborhood count associated with the candidate identifier, the updated total score neighborhood count based at least in part on the unadjusted positive-label probability and a score adjustment range, wherein the updated total score neighborhood count satisfies the neighborhood count threshold;

determine a positive score neighborhood count associated with the candidate identifier, the positive score neighborhood count based at least in part on the unadjusted positive-label probability, the score adjustment range, and a positive-label probability threshold; and generate an adjusted candidate positive-label probability associated with the candidate identifier based at least in part on the updated total score neighborhood count and the positive score neighborhood count, wherein the generated candidate positive-label probability set comprises at least one adjusted candidate positive-label probability.

20. A computer program product comprising at least one non-transitory computer-readable storage medium having computer program code thereon, the computer program code, in execution with at least one processor, configured for:

generating, based at least in part on applying a candidate selection rule set to a candidate data set, (1) a positive candidate identifier set. (2) a positive candidate index set corresponding to the positive candidate identifier set, (3) a negative candidate identifier set, (4) a negative candidate index set corresponding to the negative candidate identifier set,(5) a neutral candidate identifier set, and (6) a neutral candidate index set corresponding to the neutral candidate identifier set, wherein the candidate data set is associated with a candidate pool identifier set comprising the positive candidate identifier set, negative candidate identifier set, and neutral candidate identifier set;

training a candidate label probabilistic model based at least in part on a candidate label training subset associated with the candidate data set, wherein the candidate label training subset is identified based at least in part on (1) the positive candidate identifier set together with the positive candidate index set and a short-term record threshold, and (2) the negative candidate identifier set together with the negative candidate index set and the short-term record threshold;

generating a candidate positive-label probability set corresponding to the candidate pool identifier set based at least in part on applying an index-limited candidate data subset to the candidate label probabilistic model, wherein the index-limited candidate data subset is based at least in part on (1) the positive candidate identifier set together with the positive candidate index set and the short-term record threshold, (2) the negative candidate identifier set together with the negative candidate index set and the short-term record threshold, and (3) the neutral candidate identifier set together with the neutral candidate index set and the short-term record threshold;

training a historical record prediction model to predict the candidate positive-label probability set based at least in part on the candidate positive-label probability set and a long-term historical data subset associated with the candidate pool identifier set, wherein the long-term historical data subset is based at least in part on (1) the positive candidate identifier set together with the positive candidate index set and a long-term record threshold, (2) the negative candidate identifier set together with the negative candidate index set and the long-term record threshold, and (3) the neutral candidate identifier set together with the neutral candidate index set and the long-term record threshold; and utilizing the historical record prediction model to generate a long-term candidate positive-label probability associated with at least one candidate identifier.

* * * * *

UNITED STATES PATENT AND TRADEMARK OFFICE
CERTIFICATE OF CORRECTION

PATENT NO. : 11,537,818 B2
APPLICATION NO. : 16/746232
DATED : December 27, 2022
INVENTOR(S) : Vijay S. Nori et al.

It is certified that error appears in the above-identified patent and that said Letters Patent is hereby corrected as shown below:

In the Claims

In Column 48, Line 25, Claim 1, delete "set." and insert -- set, --, therefor.

In Column 48, Line 29, Claim 1, delete "set,(5)" and insert -- set, (5) --, therefor.

In Column 51, Line 22, Claim 6, delete "set." and insert -- set, --, therefor.

In Column 51, Line 26, Claim 6, delete "set,(5)" and insert -- set, (5) --, therefor.

In Column 55, Line 38, Claim 20, delete "set." and insert -- set, --, therefor.

In Column 55, Line 42, Claim 20, delete "set,(5)" and insert -- set, (5) --, therefor.

Signed and Sealed this
Seventh Day of March, 2023

Katherine Kelly Vidal
*Director of the United States Patent and Trademark Office*